United States Patent
Angel et al.

(10) Patent No.: US 10,301,599 B2
(45) Date of Patent: *May 28, 2019

(54) METHODS AND PRODUCTS FOR TRANSFECTION

(71) Applicant: Factor Bioscience Inc., Cambridge, MA (US)

(72) Inventors: Matthew Angel, Cambridge, MA (US); Christopher Rohde, Cambridge, MA (US)

(73) Assignee: Factor Bioscience Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/037,597

(22) Filed: Jul. 17, 2018

(65) Prior Publication Data

US 2018/0327720 A1    Nov. 15, 2018

Related U.S. Application Data

(63) Continuation of application No. 15/947,741, filed on Apr. 6, 2018, now Pat. No. 10,131,882, which is a continuation of application No. 15/844,063, filed on Dec. 15, 2017, now Pat. No. 9,969,983, which is a continuation of application No. 15/605,513, filed on May 25, 2017, now Pat. No. 9,879,228, which is a continuation of application No. 15/358,818, filed on Nov. 22, 2016, now Pat. No. 9,695,401, which is a continuation of application No. 15/178,190, filed on Jun. 9, 2016, now Pat. No. 9,562,218, which is a continuation of application No. 14/810,123, filed on Jul. 27, 2015, now Pat. No. 9,399,761, which is a continuation of application No. 13/931,251, filed on Jun. 28, 2013, now Pat. No. 9,127,248, which is a continuation of application No. 13/465,490, filed on May 7, 2012, now Pat. No. 8,497,124.

(60) Provisional application No. 61/637,570, filed on Apr. 24, 2012, provisional application No. 61/569,595, filed on Dec. 12, 2011, provisional application No. 61/566,948, filed on Dec. 5, 2011.

(51) Int. Cl.
| | |
|---|---|
| *C12N 5/00* | (2006.01) |
| *C12N 5/074* | (2010.01) |
| *C12N 5/095* | (2010.01) |
| *C12N 5/077* | (2010.01) |
| *C12N 5/071* | (2010.01) |
| *C12N 5/0789* | (2010.01) |

(52) U.S. Cl.
CPC ........ *C12N 5/0696* (2013.01); *C12N 5/0625* (2013.01); *C12N 5/0647* (2013.01); *C12N 5/0656* (2013.01); *C12N 5/0657* (2013.01); *C12N 5/0676* (2013.01); *C12N 5/0695* (2013.01); *C12N 5/0018* (2013.01); *C12N 2500/25* (2013.01); *C12N 2500/33* (2013.01); *C12N 2500/36* (2013.01); *C12N 2500/84* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2501/998* (2013.01); *C12N 2506/09* (2013.01); *C12N 2506/45* (2013.01)

(58) Field of Classification Search
CPC .......................... C12N 5/0695; C12N 5/0696
See application file for complete search history.

(56) References Cited

U.S. PATENT DOCUMENTS

| | | | |
|---|---|---|---|
| 3,539,465 A | 11/1970 | Jensen | |
| 5,843,780 A | 12/1998 | Thomson | |
| 7,442,548 B2 | 10/2008 | Thomson et al. | |
| 7,449,334 B2 | 11/2008 | Thomson et al. | |
| 7,621,606 B2 | 11/2009 | Page et al. | |
| 7,682,828 B2 | 3/2010 | Jaenisch et al. | |
| 7,687,266 B2 | 3/2010 | Chambers et al. | |
| 8,048,675 B1 | 11/2011 | Irion | |
| 8,048,999 B2 | 11/2011 | Yamanaka et al. | |
| 8,058,065 B2 | 11/2011 | Yamanaka et al. | |
| 8,071,369 B2 | 12/2011 | Jaenisch et al. | |
| 8,129,187 B2 | 3/2012 | Yamanaka et al. | |
| 2003/0083272 A1 | 5/2003 | Wiederholt et al. | |
| 2005/0053588 A1 | 3/2005 | Yin | |
| 2005/0130144 A1 | 6/2005 | Nakatsuji et al. | |
| 2008/0233610 A1 | 9/2008 | Thomson et al. | |
| 2008/0260706 A1 | 10/2008 | Rabinovich et al. | |
| 2009/0029465 A1 | 1/2009 | Thomson et al. | |
| 2009/0093433 A1 | 4/2009 | Woolf et al. | |
| 2009/0275128 A1 | 11/2009 | Thomson et al. | |
| 2009/0286852 A1 | 11/2009 | Kariko et al. | |
| 2010/0003757 A1 | 1/2010 | Mack et al. | |
| 2010/0047261 A1 | 2/2010 | Hoerr et al. | |

(Continued)

FOREIGN PATENT DOCUMENTS

| | | |
|---|---|---|
| WO | 1998030679 A1 | 7/1998 |
| WO | 2008065381 A1 | 6/2008 |

(Continued)

OTHER PUBLICATIONS

AlbuMAX I product insert (Invitrogen), (2001).

(Continued)

*Primary Examiner* — Marcia S Noble
(74) *Attorney, Agent, or Firm* — Morgan, Lewis & Bockius, LLP

(57) ABSTRACT

The present invention relates in part to methods for producing tissue-specific cells from patient samples, and to tissue-specific cells produced using these methods. Methods for reprogramming cells using RNA are disclosed. Therapeutics comprising cells produced using these methods are also disclosed.

16 Claims, 12 Drawing Sheets

Specification includes a Sequence Listing.

(56) References Cited

U.S. PATENT DOCUMENTS

| | | | |
|---|---|---|---|
| 2010/0075421 A1 | 3/2010 | Yamanaka et al. |
| 2010/0120079 A1 | 5/2010 | Page et al. |
| 2010/0144031 A1 | 6/2010 | Jaenisch et al. |
| 2010/0167286 A1 | 7/2010 | Reijo Pera et al. |
| 2010/0168000 A1 | 7/2010 | Kiessling et al. |
| 2010/0184033 A1 | 7/2010 | West et al. |
| 2010/0184227 A1 | 7/2010 | Thomson et al. |
| 2010/0221829 A1 | 9/2010 | Amit et al. |
| 2010/0233804 A1 | 9/2010 | Zhou et al. |
| 2010/0267141 A1 | 10/2010 | Shi et al. |
| 2010/0272695 A1 | 10/2010 | Agulnick et al. |
| 2010/0273220 A1 | 10/2010 | Yanki et al. |
| 2010/0304481 A1 | 12/2010 | Thomson et al. |
| 2010/0311171 A1 | 12/2010 | Nakanishi et al. |
| 2010/0317104 A1 | 12/2010 | Elefanty et al. |
| 2011/0065103 A1 | 3/2011 | Sahin et al. |
| 2011/0076678 A1 | 3/2011 | Jaenisch et al. |
| 2011/0104125 A1 | 5/2011 | Yu |
| 2011/0110899 A1 | 5/2011 | Shi et al. |
| 2011/0143397 A1 | 6/2011 | Kariko et al. |
| 2011/0143436 A1 | 6/2011 | Dahl et al. |
| 2011/0145940 A1 | 6/2011 | Voytas et al. |
| 2011/0151557 A1 | 6/2011 | Reh et al. |
| 2011/0165133 A1 | 7/2011 | Rabinovich et al. |
| 2011/0171185 A1 | 7/2011 | Klimanskaya et al. |
| 2011/0189137 A1 | 8/2011 | Rana et al. |
| 2011/0236978 A1 | 9/2011 | Stolzing et al. |
| 2011/0244566 A1 | 10/2011 | Wu et al. |
| 2011/0263015 A1 | 10/2011 | D'Costa et al. |
| 2012/0046346 A1 | 2/2012 | Rossi et al. |
| 2012/0202291 A1 | 8/2012 | Chen et al. |
| 2012/0301455 A1 | 11/2012 | Hunt |
| 2013/0071365 A1 | 3/2013 | Suzuki |
| 2013/0189327 A1 | 7/2013 | Ortega et al. |
| 2013/0189741 A1 | 7/2013 | Meis et al. |
| 2014/0242595 A1 | 8/2014 | Yu et al. |

FOREIGN PATENT DOCUMENTS

| | | |
|---|---|---|
| WO | 2009147400 A1 | 12/2009 |
| WO | 2010093655 A2 | 8/2010 |
| WO | 2011110886 A1 | 9/2011 |
| WO | 2011114237 A2 | 9/2011 |
| WO | 2011012316 A2 | 10/2011 |
| WO | 2011140397 A2 | 11/2011 |
| WO | 2012019122 A2 | 2/2012 |
| WO | 2012036299 A1 | 3/2012 |
| WO | 2012060473 A1 | 5/2012 |
| WO | 2012122318 A2 | 9/2012 |

OTHER PUBLICATIONS

Anderson et al., "Incorporation of pseudouridine into mRNA entrances translation by diminishing PKR activation," Nucl. Acids Res. 38(17): 5884-5892 (2010).

Anderson et al., "Nucleoside modifications in RNA limit activation of 2'-5'-oligoadenylate synthetase and increase resistance to cleavage by RNase L," Nucl. Acids Res. 39(21):9329-9338 (2011).

Anderson et al., "Nucleofection induces transient eIF2α phosphorylahon by GCN2 and PERK6," Gene Ther. 1-7 (epub ahead of print) (2012).

Angel, "Extended Transient Transfection by Repeated Delivery of an In Vitro-Transcribed RNA," Master of Science in Electrical Engineering and Computer Science, 56 pages (Massachusetts Institute of Technology, Cambridge, Massachusetts) (2009).

Angel, "Reprogramming human somatic cells to pluripotency using RNA," Doctor of Philosophy in Electrical Engineering and Computer Science, 55 pages (Massachusetts Institute of Technology, Cambridge, Massachusetts) (2011).

Angel, Matthew "Reprogramming Human Somatic Cells to Pluripotency Using RNA" (PhD diss., Massachusetts Institute of Technology) (2012).

Angel and Yanik,. "Innate Immune Suppression Enables Frequent Transtection with RNA Encoding Reprogramming Proteins," PLoS ONE 5(7):e11756, 7 pages (2010).

Arnold et al., "Reprogramming of Human Huntington Fibroblasts Using mRNA," ISRN Cell Biology 2012: Article ID 124878, 12 pages (2012).

Barker and Nienhuts, "A method for the deionization of bovine serum albumin," Tissue Culture Association, 2 pages (1975).

Bolli et al., "Cardiac stem cells in patients with ischaemic cardiomyopathy (SCIPIO): initial results of a randomised phase 1 trial," Lancet 378:1847-1857 (2011).

Braam et al., "Recombinant vitronectin is a functionally defined substrate that supports human embryonic stem cell self-renewal via αv β5 integrin," Stem Cells 26:2257-2265 (2008).

Chen et al., "Chemically defined conditions for human iPSC derivation and culture," Nat. Methods 8:424-429 (2011).

Chen et al., "Rational optimization of reprogramming culture conditions for the generation of induced pluripotent stem cells with ultra-high efficiency and fast kinetics," Cell Research 21:884-894 (2011).

Droge et al., "A comparative study of some physico-ohemical properties of human serum albumin samples from different sources—I. Some physico-chemical properties of isoionic human serum albumin solutions," Biochem. Pharmacol. 31:3775-3779 (1982).

Ete et al., "Conversion of mouse fibroblasts into cardiomyocytes using a direct reprogramming strategy," Nat. Cell Biol. 13:215-222 (2011).

Garcia-Gonzalo and Izpisua Belmonte, "Albumin-associated lipids regulate human embryonic stem cell self-renewal," PLoS One 3:e1384 (2008).

Goldberg and Rabinowitz, "The incorporation of 5-ribosyluracil triphosphate into RNA in nuclear extracts of mammalian cells," Biochem. Biophys. Res. Commun. 6:394-398 (1961).

International Search Report dated Apr. 11, 2013, in PCT/2012/067966 (3 pages).

Kariko et al., "In vivo protein expression from mRNA delivered into adult rat brain," J. Neurosci. Methods 105:77-86 (2001).

Kariko et al., "mRNA is an endogenous ligand for Toll-like receptor 3," J. Biol, Chem. 279:12542-12550 (2004).

Kariko et al., "Suppression of RNA recognition by Toll-like receptors: the impact of nucleoside modification and the evolutionary origin of RNA," Immunity 23:165-175 (2005).

Kariko et al., "Incorporation oil pseudouridine into mRNA yields superior nonimmunogenic vector with increased translational capacity and biological stability," Mol. Ther. 16:1833-1840 (2008).

Kariko et al., "Generating the optimal mRNA for therapy; HPLC purification eliminates immune activation and improves translation of nucleoside-modified, protein-encoding mRNA," Nucl. Acids Res. 39:e142 (2011).

Kariko et al., "Increased Erythropoesis in Mice Injected With Subnricrogram Quantities of Pseudouridine-containing mRNA Encoding Erythropoietin," Mol. Ther. 20:948-953 (2012).

Kim et al., "Pluripotent stem cells induced from adult neural stem cells by reprogramming with two factors," Nature 454:646-650 (2008).

Kim et al., "Oct4-inclued pluripotency in adult neural stem cells," Cell 136:411-419 (2009).

Kim et al., "Direct reprogramming of human neural stem cells by OCT4," Nature 461:649-653 (2009).

Lu, et al., "Defined culture conditions of human embryonic stern cells" PNAS; 103;5688-5693 (2006).

Ludwig et al., "Feeder-independent culture of human embryonic stern cells," Nat. Methods 3:637-646 (2006).

Ludwig et al., "Derivation of human embryonic stem cells in defined conditions," Nat. Biotechnol. 24:185-187 (2006).

MIT Thesis Record, "Reprogramming human somatic cells to pluripotency using RNA," (Matthew Angel, author), (2012).

Ng et al., "A protocol describing the use of a recombinant protein-based, animal product-free medium (APEL) for human embryonic stern cell differentiation as spin embryoid bodies," Nat. Protoc. 3:768-776 (2008).

(56) References Cited

OTHER PUBLICATIONS

Plews et al., "Activation of pluripotency genes in human fibroblast cells by a novel mRNA based approach," PLoS One 5:e14397 (2010).
Schneider, "An Effective Method for Defatting Albumin Using Resin Columns," Biochem. Biophys. Acta, 221, 376-318, (1970).
Schwartz et al., "Embryonic stem cell trials for macular degeneration: a preliminary report," Lancet 379:713-720 (2012).
Takahashi and Yamanaka "Induction of pluripotent stem cells from mouse embryonic and adult fibroblast cultures by defined factors," Cell 126:663-676 (2006).
Takahashi et al., "Induction of plunpotent stem cells from adult human fibroblasts by defined factors,"Cell 131:861-872(2007).
Warren et al., "Highly efficient reprogramming to pluripotency and directed differentiation of human cells with synthetic modified mRNA," Cell Stem Cell 7:618-630(2010).
Yakubov et al., "Reprogramming of human fibroblasts to pluripotent stem cells using mRNA of four transcription factors," Biochem. Biophys. Res. Commun. 394:189-193 (2010).
Yu et al., "Induced pluripotent stem cell lines derived from human somatic cells," Science 318:1917-1920(2007).
"Xeno-Free System tor hESC & hiPSG. Facilitating the Shift from Stem Cell Research to Clinical Applications," 12 pages, Biological Industries Catalog (Stem Cell Products) (2011).

SEQUENCE LISTING

<160> NUMBER OF SEQ ID NOS: 4

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Pro Glu Pro Gly Trp Val Asp Pro
            20                  25                  30

Arg Thr Trp Leu Ser Phe Gln Gly Pro Gly Gly Pro Gly Ile Gly
            35                  40                  45

Pro Gly Val Gly Pro Gly Ser Glu Val Trp Gly Ile Pro Pro Cys Pro
50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
            85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
            165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
            210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
            245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
            325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 2
<211> LENGTH: 317
<212> TYPE: PRT
<213> ORGANISM: Homo sapiens

<400> SEQUENCE: 2

Met Tyr Asn Met Met Glu Thr Glu Leu Lys Pro Pro Gly Pro Gln Gln
1                   5                   10                  15

Thr Ser Gly Gly Gly Gly Gly Asn Ser Thr Ala Ala Ala Ala Gly Gly

```
                    20                  25                  30
Asn Gln Lys Asn Ser Pro Asp Arg Val Lys Arg Pro Met Asn Ala Phe
                35                  40                  45

Met Val Trp Ser Arg Gly Gln Arg Lys Met Ala Gln Glu Asn Pro
 50                  55                  60

Lys Met His Asn Ser Glu Ile Ser Lys Arg Leu Gly Ala Glu Trp Lys
 65                  70                  75                  80

Leu Leu Ser Glu Thr Glu Lys Arg Pro Phe Ile Asp Glu Ala Lys Arg
                 85                  90                  95

Leu Arg Ala Leu His Met Lys Glu His Pro Asp Tyr Lys Tyr Arg Pro
                100                 105                 110

Arg Arg Lys Thr Lys Thr Leu Met Lys Lys Asp Lys Tyr Thr Leu Pro
                115                 120                 125

Gly Gly Leu Leu Ala Pro Gly Gly Asn Ser Met Ala Ser Gly Val Gly
                130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
                180                 185                 190

Gln Met Gln Pro Met His Arg Tyr Asp Val Ser Ala Leu Gln Tyr Asn
                195                 200                 205

Ser Met Thr Ser Ser Gln Thr Tyr Met Asn Gly Ser Pro Thr Tyr Ser
210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Pro Pro Val Val Thr
                245                 250                 255

Ser Ser Ser His Ser Arg Ala Pro Cys Gln Ala Gly Asp Leu Arg Asp
                260                 265                 270

Met Ile Ser Met Tyr Leu Pro Gly Ala Glu Val Pro Glu Pro Ala Ala
                275                 280                 285

Pro Ser Arg Leu His Met Ser Gln His Tyr Gln Ser Gly Pro Val Pro
                290                 295                 300

Gly Thr Ala Ile Asn Gly Thr Leu Pro Leu Ser His Met
305                 310                 315

<210> SEQ ID NO 3
<211> LENGTH: 479
<212> TYPE: PRT
<213> ORGANISM: Homo sapiens

<400> SEQUENCE: 3

Met Arg Gln Pro Pro Gly Glu Ser Asp Met Ala Val Ser Asp Ala Leu
 1               5                  10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
                35                  40                  45

Ser His Met Lys Arg Leu Pro Pro Val Leu Pro Gly Arg Pro Tyr Asp
                50                  55                  60

Leu Ala Ala Ala Thr Val Ala Thr Asp Leu Glu Ser Gly Gly Ala Gly
 65                  70                  75                  80
```

```
Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Pro Ser Ser Gly Pro Ala Ser Ala
130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Leu Leu Tyr Gly Arg Glu
                165                 170                 175

Ser Ala Pro Pro Pro Thr Ala Pro Phe Asn Leu Ala Asp Ile Asn Asp
                180                 185                 190

Val Ser Pro Ser Gly Gly Phe Val Ala Glu Leu Leu Arg Pro Glu Leu
                195                 200                 205

Asp Pro Val Tyr Ile Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
                260                 265                 270

Thr Cys Pro Lys Ile Lys Gln Glu Ala Val Ser Ser Cys Thr His Leu
                275                 280                 285

Gly Ala Gly Pro Pro Leu Ser Asn Gly His Arg Pro Ala Ala His Asp
        290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
                340                 345                 350

Pro Asp Gln Met Gln Pro Gln Val Pro Pro Leu His Tyr Gln Glu Leu
            355                 360                 365

Met Pro Pro Gly Ser Cys Met Pro Glu Glu Pro Lys Pro Lys Arg Gly
            370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430

Cys Gly Trp Lys Phe Ala Arg Ser Asp Glu Leu Thr Arg His Tyr Arg
            435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 4
<211> LENGTH: 454
<212> TYPE: PRT
```

<213> ORGANISM: Homo sapiens

<400> SEQUENCE: 4

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

```
-continued

Asn Asn Glu Lys Ala Pro Lys Val Val Ile Leu Lys Lys Ala Thr Ala
            405             410             415

Tyr Ile Leu Ser Val Gln Ala Glu Glu Gln Lys Leu Ile Ser Glu Glu
            420             425             430

Asp Leu Leu Arg Lys Arg Arg Glu Gln Leu Lys His Lys Leu Glu Gln
            435             440             445

Leu Arg Asn Ser Cys Ala
    450
```

METHODS AND PRODUCTS FOR TRANSFECTION

The present application is a continuation of U.S. patent application Ser. No. 15/947,741, filed Apr. 6, 2018, which is a continuation of U.S. patent application Ser. No. 15/844,063, filed Dec. 15, 2017 (now U.S. Pat. No. 9,969,983), which is a continuation of U.S. patent application Ser. No. 15/605,513, filed May 25, 2017 (now U.S. Pat. No. 9,879,228), which is a continuation of U.S. patent application Ser. No. 15/358,818, filed Nov. 22, 2016 (now U.S. Pat. No. 9,695,401), which is a continuation of U.S. patent application Ser. No. 15/178,190, filed on Jun. 9, 2016 (now U.S. Pat. No. 9,562,218), which is a continuation of U.S. patent application Ser. No. 14/810,123, filed Jul. 27, 2015 (now U.S. Pat. No. 9,399,761), which is a continuation of U.S. patent application Ser. No. 13/931,251, filed on Jun. 28, 2013 (now U.S. Pat. No. 9,127,248), which is a continuation of U.S. patent application Ser. No. 13/465,490, filed on May 7, 2012 (now U.S. Pat. No. 8,497,124), which claims priority to and benefit of U.S. Provisional Application No. 61/566,948, filed on Dec. 5, 2011, U.S. Provisional Application No. 61/569,595, filed on Dec. 12, 2011, and U.S. Provisional Application No. 61/637,570, filed on Apr. 24, 2012, each of which are hereby incorporated by reference in their entireties.

FIELD OF THE INVENTION

The present invention relates in part to methods for delivering nucleic acids to cells, and to therapeutics comprising cells produced using these methods.

SEQUENCE LISTING

The instant application contains a Sequence Listing which has been submitted in ASCII format via EFS-Web and is hereby incorporated by reference in its entirety. Said ASCII copy, recorded Jul. 17, 2018, is named "FAB-003C8_Sequence_Listing_.txt" and is 14,702 bytes in size.

BACKGROUND

Nucleic-Acid Transfection

Nucleic acids can be delivered to cells both in vitro and in vivo by pre-complexing the nucleic acids with charged lipids, lipidoids, peptides, polymers or mixtures thereof. Such transaction reagents are commercially available, and are widely used for delivering nucleic acids to cells in culture. Cells exposed to transfection reagent-nucleic acid complexes may internalize these complexes by endocytosis or other means. Once inside a cell, the nucleic acid can carry out its intended biological function. In the case of protein-encoding RNA, for example, the RNA can be translated into protein by the ribosomes of the cell.

Many variables can affect the efficiency of reagent-based transfection, including the structure of the transfection reagent, the concentration of the nucleic acid, and the complex-formation time. Designing a transfection protocol is made even more difficult by the fact that adjusting these variables to increase transfection efficiency often increases transfection-associated toxicity. In addition, several common components of cell-culture media, including serum, some antibiotics, and polyanions such as dextran sulfate or heparin, can inhibit transfection and/or cause cell death when cells are transacted in media containing these components. Thus, the composition of the Transfection medium is a critical factor in determining both transfection efficiency and transfection-associated toxicity.

Serum-Free Cell Culture

Animal sera such as fetal bovine serum (FBS) are commonly used as a supplement in cell-culture media to promote the growth of many types of cells. However, the undefined nature of serum makes cells that are contacted with this component, undesirable for both research and therapeutic applications. As a result, serum-free cell-culture media have been developed to eliminate the batch-to-batch variability and the risk of contamination with toxic and/or pathogenic substances that are associated with serum.

The most abundant protein in serum is serum albumin. Serum albumin binds to a wide variety of molecules both in vitro and in vivo, including hormones, fatty acids, calcium and metal ions, and small-molecule drugs, and transports these molecules to cells, both in vitro and in vivo. Serum albumin (most often either bovine serum albumin (BSA) or human serum albumin (HSA)) is a common ingredient in serum-free cell-culture media, where it is typically used at a concentration of 3-10 g/L. Serum albumin is traditionally prepared from blood plasma by ethanol fractionation (the "Colin" process). The fraction containing serum albumin ("Cohn Fraction V" or simply "Fraction V") is isolated, and is typically used without further treatment. Thus, standard preparations of serum albumin comprise a protein part (the serum albumin polypeptide) and an associated-molecule part (including salts, fatty acids, etc. that are bound to the serum albumin polypeptide). The composition of the associated-molecule component of serum albumin is, in general, complex and unknown.

Serum albumin can be treated for use in certain specialized applications[1-3] (U.S. Patent Appl. Pub. No. U.S. 2010/0168000 A1). These treatment processes are most commonly used to remove globulins and contaminating viruses from solutions of scrum albumin, and often include stabilization of the serum albumin polypeptide by addition of the short-chain fatty acid, octanoic acid, followed by heat-inactivation/precipitation of the contaminants. For highly specialized stem-cell-culture applications, using an ion-exchange resin to remove excess salt from solutions of BSA has been shown to increase cell viability[3]. However, recombinant serum albumin does not benefit from such treatment, even in the same sensitive stem-cell-culture applications[3], demonstrating that the effect of deionization in these applications is to remove excess salt from the albumin solution, and not to alter the associated-molecule component of the albumin, in addition, the effect of such treatment on other cell types such as human fibroblasts, and the effect of such treatment on transfection efficiency and transfection-associated toxicity have not been previously explored. Furthermore, albumin-associated lipids have been shown to be critical for human pluripotent stem-cell culture, and removing these from albumin has been shown to result in spontaneous differentiation of human pluripotent stem cells, even when lipids are added separately to the cell-culture medium[4]. Thus, a cell-culture medium containing albumin with an unmodified associated-molecule component is thought to be critical for the culture of human pluripotent stem cells. Importantly, the relationship between the associated-molecule component of lipid carriers such as albumin and transection efficiency and transfection-associated toxicity has not been previously explored.

Cell Reprogramming

Cells can be reprogrammed by exposing them to specific extracellular cues and/or by ectopic expression of specific proteins, microRNAs, etc.[5-9] While several reprogramming methods have been previously described, most that rely on ectopic expression require the introduction of exogenous DNA, which carries mutation risks. These risks make DMA-based reprogramming methods undesirable for therapeutic applications. DNA-free reprogramming methods based on direct delivery of reprogramming proteins have been reported[10, 11], however these techniques are too inefficient and unreliable for commercial use. In addition, RNA-based reprogramming methods have been described[12-15], however, all previously disclosed RNA-based reprogramming methods are slow, unreliable, and inefficient when applied to adult cells, require many transections (resulting in significant expense and opportunity for error), can reprogram only a limited number of cell types, can reprogram cells to only a limited number of cell types, require the use of immunosuppressants, and require the use of multiple human-derived components, including blood-derived HSA and human fibroblast feeders. The many drawbacks of previously disclosed RNA-based reprogramming methods make them undesirable for both research and therapeutic use.

Cell-Based Therapeutics

Many diseases are caused by the loss of or damage to one or more tissue-specific cells. Methods for treating such diseases by replacing the lost or damaged cells with cells taken from animals or from one or more human donors have been described. However, the critical shortage of donor cells represents a barrier to the development of cell-based therapeutics for most diseases. In addition, therapeutics based on the use of cells from non-isogenic donors or animals carry a risk of rejection. As a result patients receiving such cells must fake strong immunosuppressant drugs, which themselves carry serious side-effects.

SUMMARY OF THE INVENTION

Here we describe reagents and protocols for transfecting and reprogramming cells. Unlike previously reported methods, certain embodiments of the present invention do not involve exposing the cells to exogenous DNA or to allogeneic or animal-derived materials, making reagents and cells produced according to the methods of the present invention useful for therapeutic applications.

We disclose methods for treating albumin for use in transfection, and we provide a cell-culture medium for high-efficiency transfection and reprogramming of cells. We further disclose therapeutics comprising cells that are reprogrammed according to the methods of the present invention, including for the treatment of type 1 diabetes, heart disease, including ischemic and dilated cardiomyopathy, macular degeneration, Parkinson's disease, cystic fibrosis, sickle-cell anemia, thalassemia, Fanconi anemia, severe combined immunodeficiency, hereditary sensory neuropathy, xeroderma pigmentosum, Huntington's disease, muscular dystrophy, amyotrophic lateral sclerosis, Alzheimer's disease, and HIV/AIDS.

DETAILED DESCRIPTION OF THE FIGURES

The present invention is illustrated by way of example, and not by way of limitation, in the figures of the accompanying drawings and in which.

Figure 3:
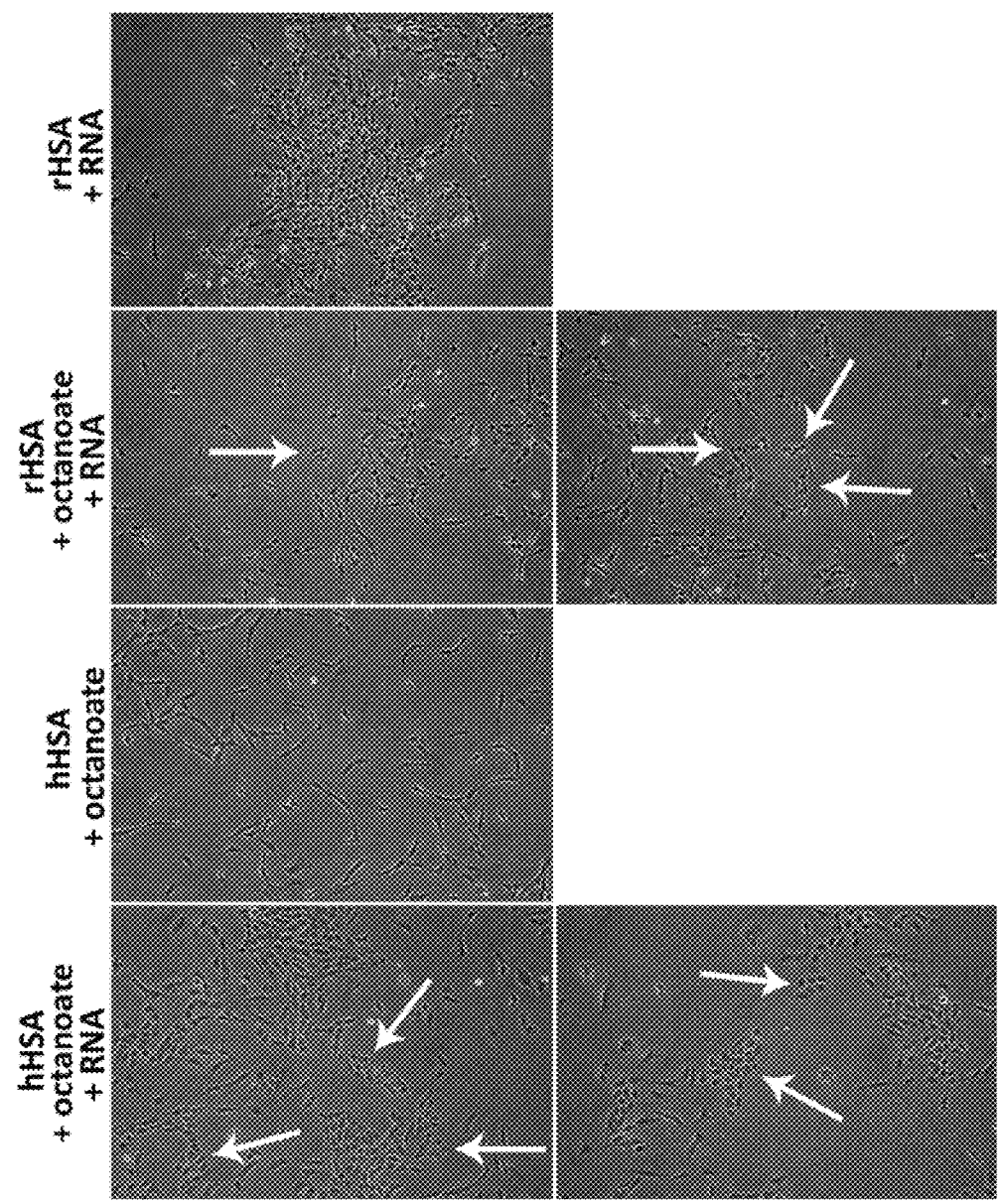

FIG. 3 depicts primary human fibroblasts cultured m media containing the indicated HSA. "+ RNA" indicates that the cells were transfected daily with a mixture of RNA encoding Oct4, Sox2, Klf4, c-Myc-2 (T58A), and Lin28 beginning on day 0. Pictures were taken on day 3. Arrows indicate areas of morphological changes indicative of reprogramming.

Figure 4:
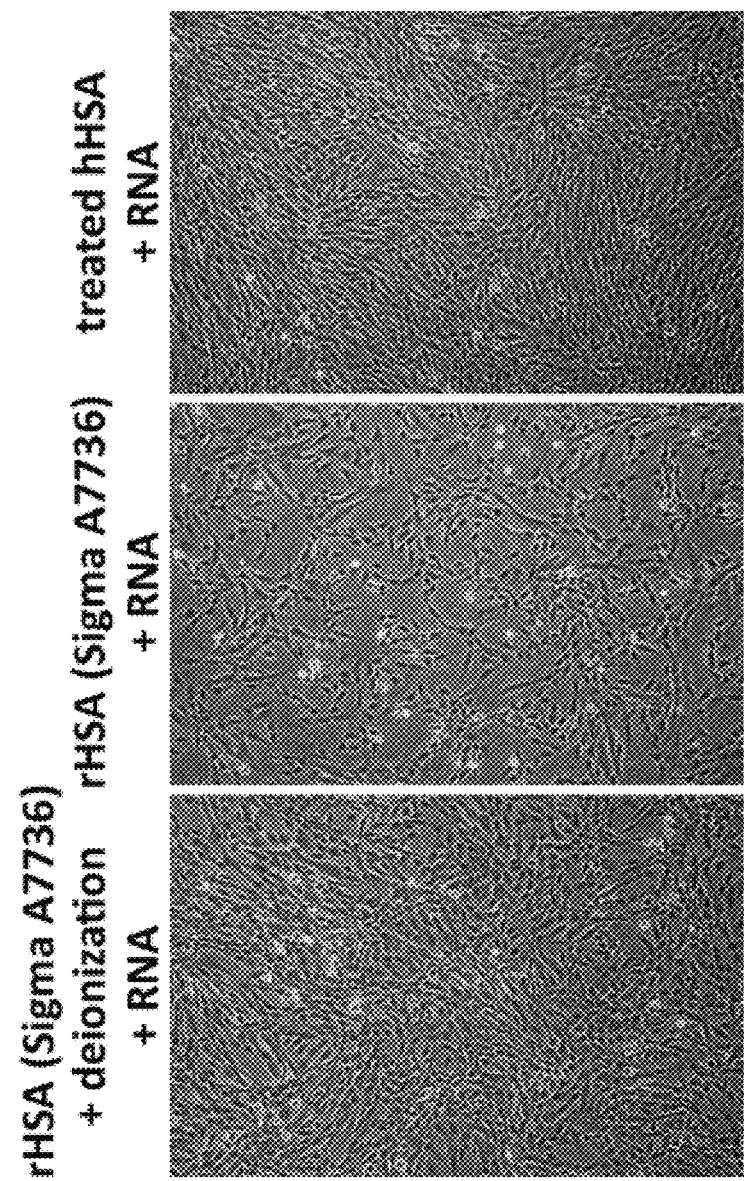

FIG. 4 depicts primary human fibroblasts cultured its media containing the indicated HSA, and transfected daily with a mixture of RNA encoding the proteins Oct4, Sox2, Klf4, c-Myc-2 (T58A), and Lin28 beginning on day 0. Pictures were taken on day 2.

Figure 5:
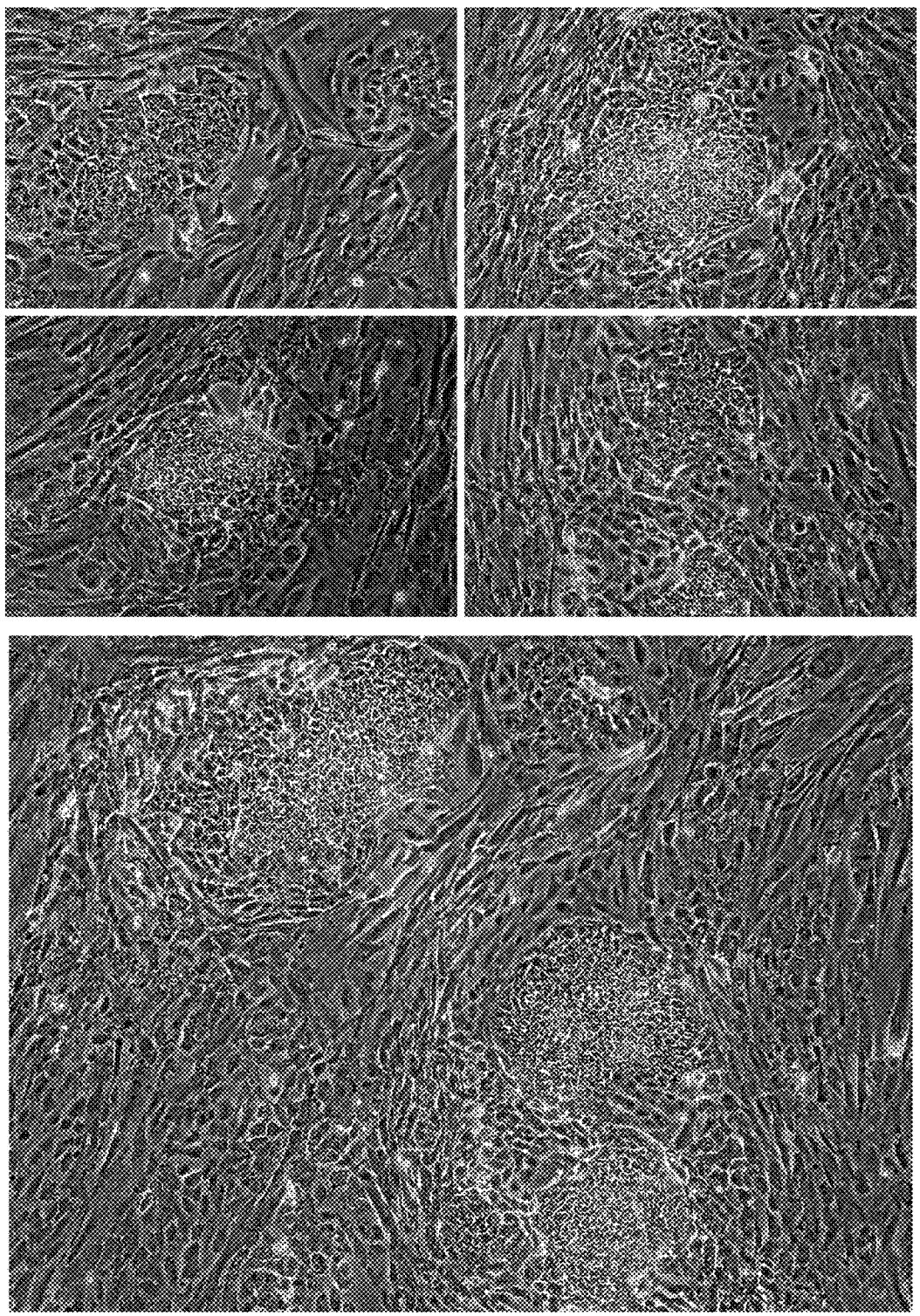

FIG. 5 depicts primary human fibroblasts transfected daily with RNA encoding the proteins Oct4, Sox2, Klf4, c-Myc-2 (T58A), and Lin28, beginning on day 0, Pictures were taken on day 10, Large colonies of cells with a reprogrammed morphology are visible in each picture. The bottom panel depicts a representative field, showing a high density of reprogrammed cells, indicating high-efficiency reprogramming.

Figure 6:
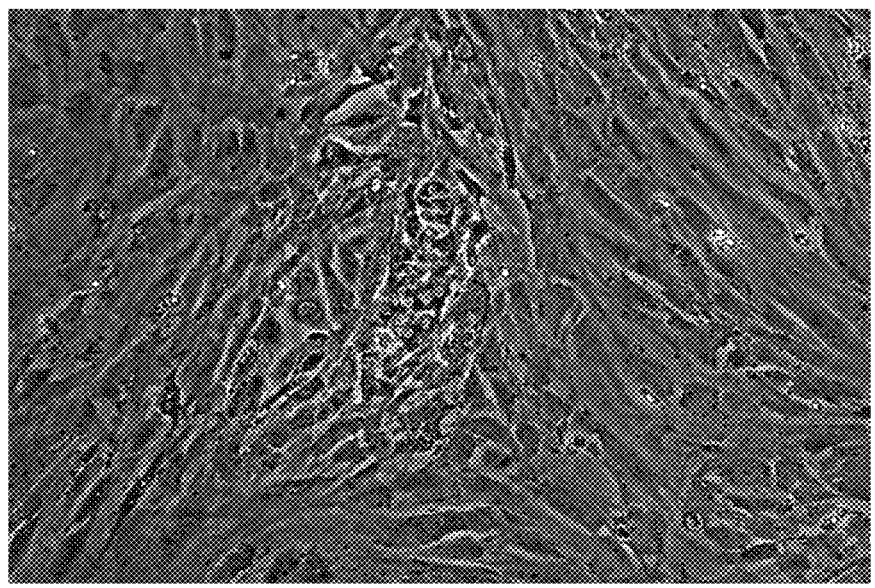

FIG. 6 depicts primary human fibroblasts transfected and cultured as in FIG. 5, but without using feeders or immunosuppressants. A total of 5 transfections were performed. Pictures were taken on day 7. A small colony of cells with a reprogrammed morphology is visible in the center of the picture.

Figure 7:
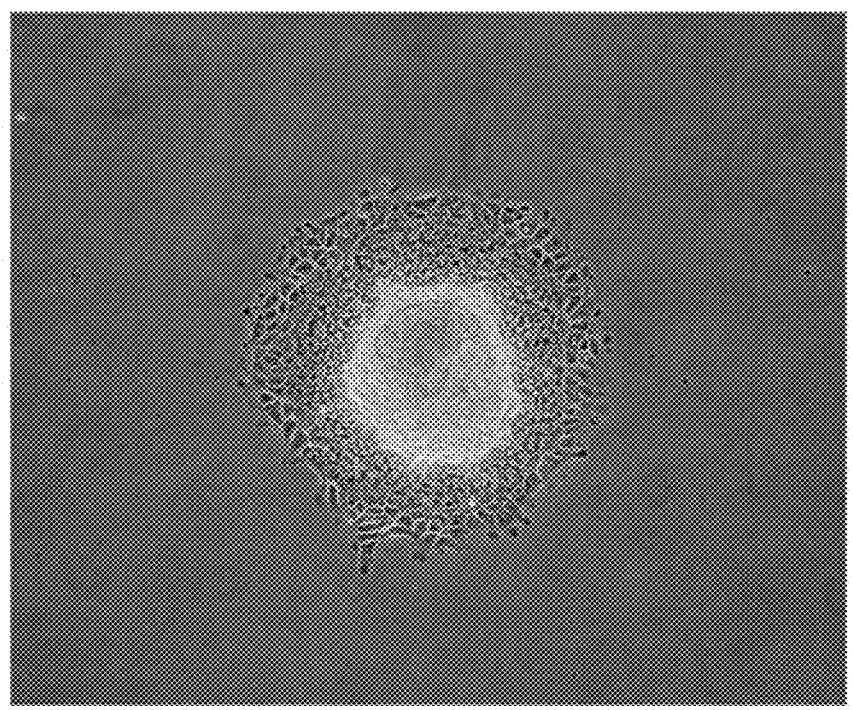

FIG. 7 depicts a reprogrammed cell line one day after colonies were picked and plated on a basement membrane extract-coated plate.

Figure 8:
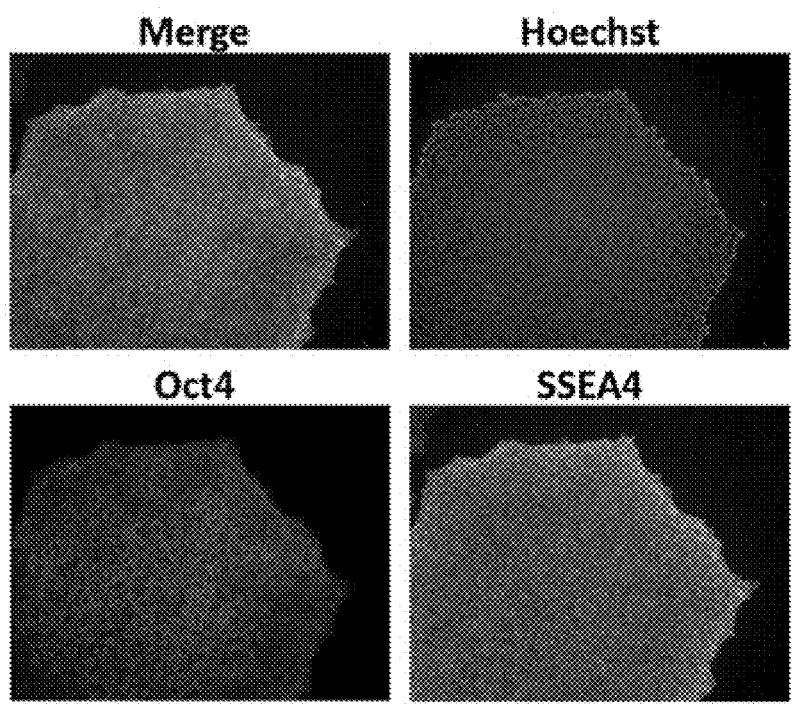

FIG. 8 depicts a reprogrammed cell line stained for the pluripotent stem-cell markers Oct4 and SSEA4. The panel labeled "Hoechst" shows the nuclei, and the panel labeled "Merge" shows the merged signals from the three channels.

Figure 9:
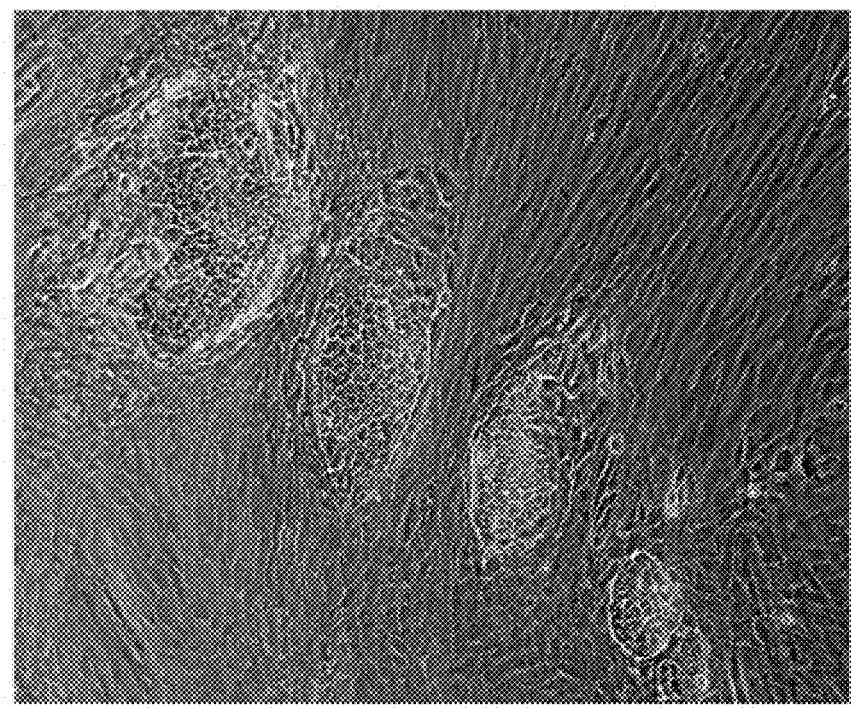

FIG. 9 depicts primary human fibroblasts transfected and cultured as in FIG. 6. A total of 5 transfections were performed. Pictures were taken on day 7. Several colonies of cells with a reprogrammed morphology are visible.

Figure 10A:
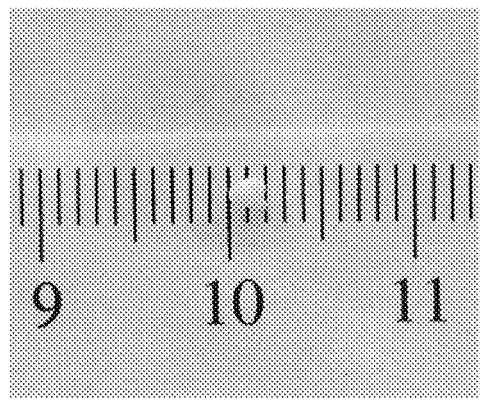

FIG. 10A depicts a 1.5 mm-diameter dermal punch biopsy tissue sample.

Figure 10B:
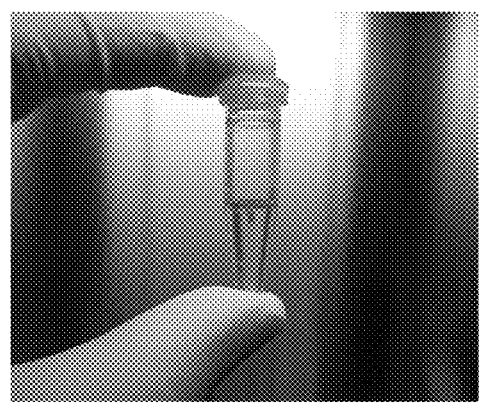

FIG. 10B depicts a tissue sample harvested as in FIG. 10A, and suspended at the air-liquid interface of a solution containing an enzyme.

Figure 10C:
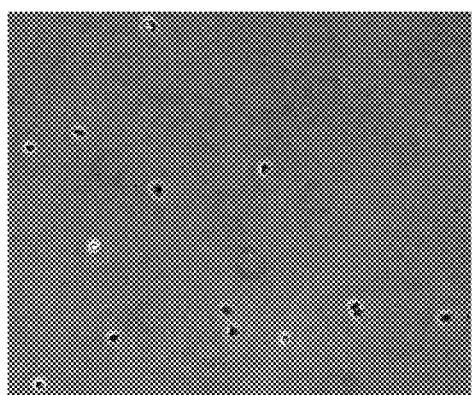

FIG. 10C depicts primary human fibroblasts harvested as in FIG. 10A, dissociated as in FIG. 10B, and plated in a well of a 96-well plate.

Figure 11:
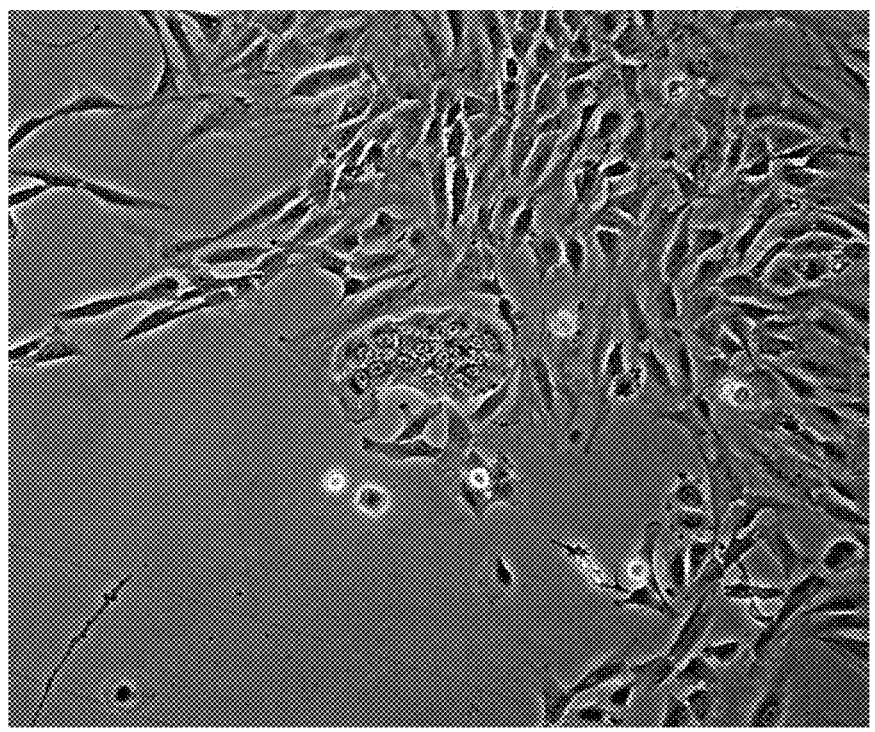

FIG. 11 depicts primary human fibroblasts prepared as in FIG. 10C, and reprogrammed using RNA.

Figure 12:
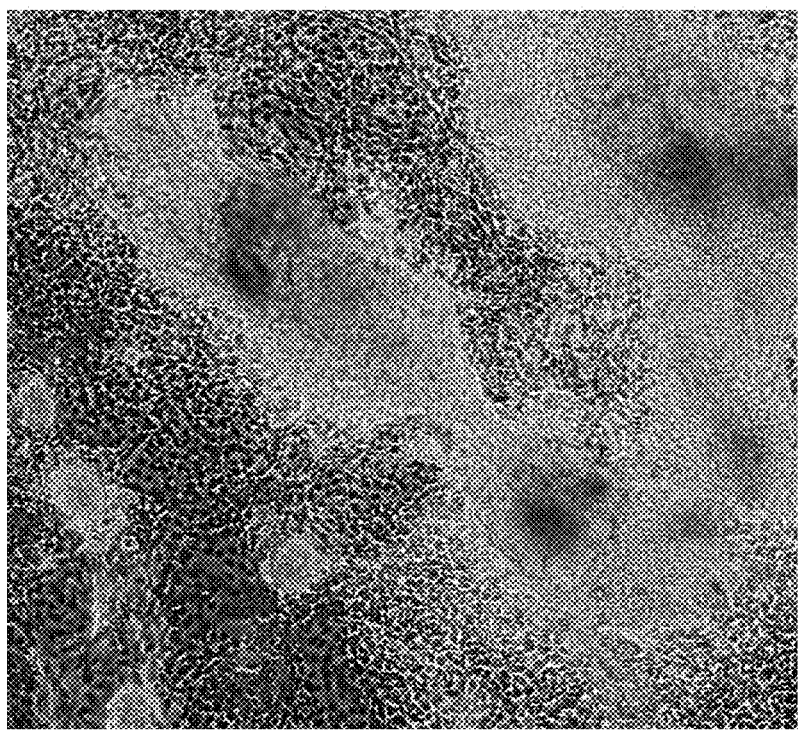

FIG. 12 depicts cardiac cells generated by reprogramming primary human fibroblasts using the methods of the present invention.

DEFINITIONS

By "molecule" is meant a molecular entity (molecule, ion, complex, etc.).

By "RNA molecule" is meant a molecule that comprises RNA.

By "synthetic RNA molecule" is meant an RNA molecule that is produced outside of a cell, for example, an RNA molecule that is produced in an in vitro-transcription reaction or an RNA molecule that is produced by direct chemical synthesis.

By "transfection" is meant contacting a cell with a molecule, wherein the molecule is internalized by the cell.

By "transfection reagent" is meant a substance or mixture of substances that associates with a molecule and facilitates the delivery of the molecule to and/or internalization of the molecule by a cell, for example, a cationic lipid, a charged polymer or a cell-penetrating peptide.

By "reagent-based transfection" is meant transfection using a transfection reagent.

By "cell-culture medium" is meant a medium that can be used for cell culture, for example, Dulbecco's Modified Eagle's Medium (DMEM) or DMEM+10% fetal bovine serum (FBS).

By "complexation medium" is meant a medium to which a transfection reagent and a molecule to be transfected are added and in which the transfection reagent associates with the molecule to be transfected.

By "transfection medium" is meant a medium that can be used for transfection, for example, Dulbecco's Modified Eagle's Medium (DMEM) or DMEM/F12.

By "recombinant" is meant a protein or peptide that is not produced in animals or humans, for example, human transferrin that is produced in bacteria, human fibronectin that is produced in an in vitro culture of mouse cells or human serum albumin that is produced in a rice plant.

By "lipid carrier" is meant a substance that increases the solubility of a lipid or lipid-soluble molecule in an aqueous solution, for example, human serum albumin or methyl-beta-cyclodextrin.

By "Oct4 protein" is meant a protein that is encoded by the POU5F1 gene, or a natural or engineered variant, family-member, orthologue, fragment or fusion construct thereof, for example, human Oct4 protein (SEQ ID NO: 1), mouse Oct4 protein, Oct1 protein, a protein encoded by POU5F1 pseudogene 2, a DMA-binding domain of Oct4 protein or an Oct4-GFP fusion protein. In some embodiments the Oct4 protein comprises an amino acid sequence that has at least 70% identity with SEQ. ID NO:1, or in other embodiments, at least 75%, 80%, 85%, 90%, or 95% identity with SEQ ID NO:1. In some embodiments, the Oct4 protein comprises an amino acid sequence having from 1 to 20 amino acid insertions, deletions, or substitutions (collectively) with respect to SEQ ID NO:1. Or in other embodiments, the Oct4 protein comprises an amino acid sequence having from 1 to 15 or from 1 to 10 amino acid insertions, deletions, or substitutions (collectively) with respect to SEQ ID NO: 1.

By "Sox2 protein" is meant a protein that is encoded by the SOX2 gene, or a natural or engineered variant, family-member, orthologue, fragment or fusion construct thereof, for example, human Sox2 protein (SEQ ID NO: 2), mouse Sox2 protein, a DMA-binding domain of Sox2 protein or a Sox2-GFP fusion protein. In some embodiments the Sox2 protein comprises an amino acid sequence that has at least 70% identity with SEQ ID NO:2, or in other embodiments, at least 75%, 80%, 85%, 90%, or 95% identity with SEQ ID NO:2. In some embodiments, the Sox2 protein comprises an amino acid sequence having from 1 to 20 amino acid insertions, deletions, or substitutions (collectively) with respect to SEQ ID NO:2. Or in other embodiments, the Sox2 protein comprises an amino acid sequence having from 1 to 15 or from 1 to 10 amino acid insertions, deletions, or substitutions (collectively) with respect to SEQ ID NO:2.

By "Klf4 protein" is meant a protein that is encoded by the KLF4 gene, or a natural or engineered variant, family-member, orthologue, fragment or fusion construct thereof, for example, human Klf4 protein (SEQ ID NO: 3), mouse Klf4 protein, a DNA-binding domain of Klf4 protein or a Klf4-GFP fusion protein. In some embodiments the klf4 protein comprises an amino acid sequence that has at least 70% identity with SEQ ID NO:3, or in other embodiments, at least 75%, 80%, 85%, 90%, or 95% identity with SEQ ID NO:3. In some embodiments, the klf4 protein comprises an amino acid sequence having from 1 to 20 amino acid insertions, deletions, or substitutions (collectively) with respect to SEQ ID NO:3. Or in other embodiments, the klf4 protein comprises an amino acid sequence having from 1 to 15 or from 1 to 10 amino acid insertions, deletions, or substitutions (collectively) with respect to SEQ ID NO:3.

By "c-Myc protein" is meant a protein that is encoded by the MYC gene, or a natural or engineered variant, family-member, orthologue, fragment or fusion construct thereof, for example, human c-Myc protein (SEQ ID NO: 4), mouse c-Myc protein, l-Myc protein, c-Myc (T58A) protein, a DNA-binding domain of c-Myc protein or a c-Myc-GFP fusion protein. In some embodiments the c-Myc protein comprises an amino acid sequence that has at least 70% identity with SEQ ID NO:4, or in other embodiments, at least 75%, 80%, 85%, 90%, or 95% identity with SEQ ID NO:4. In some embodiments, the c-Myc protein comprises an amino acid having from 1 to 20 amino acid insertions, deletions, or substitutions (collectively) with respect to SEQ ID NO:4. Or in other embodiments, the c-Myc protein comprises an amino acid sequence having from 1 to 15 or from 1 to 10 amino acid insertions, deletions, or substitutions (collectively) with respect to SEQ ID NO:4.

By "reprogramming" is meant causing a change in the phenotype of a cell, for example, causing a β-cell progenitor to differentiate into a mature β-cell, causing a fibroblast to dedifferentiate into a pluripotent stem cell, causing a keratinocyte to transdifferentiate into a cardiac stem cell or causing the axon of a neuron to grow.

By "reprogramming factor" is meant a molecule that, when a cell is contacted with the molecule or the cell expresses the molecule, can, either alone or in combination with other molecules, cause reprogramming, for example, Oct4 protein.

By "feeder" is meant a cell that is used to condition medium or to otherwise support the growth of other cells in culture.

By "conditioning" is meant contacting one or more feeders with a medium.

By "fatty acid" is meant a molecule that, comprises an aliphatic chain of at least two carbon atoms, for example, linoleic acid, α-linolenic acid, octanoic acid, a leukotriene, a prostaglandin, cholesterol, a resolvin, a protectin, a thromboxane, a lipoxin, a maresin, a sphingolipid, tryptophan, N-acetyl tryptophan or a salt, methyl ester or derivative thereof.

By "short-chain fatty acid" is meant a fatty acid that comprises an aliphatic chain of between two and 30 carbon atoms.

By "albumin" is meant a protein that is highly soluble in water, for example, human serum albumin.

By "associated molecule" is meant a molecule that is non-covalently bound to another molecule.

By "associated-molecule-component of albumin" is meant one or more molecules that are bound to an albumin polypeptide, for example, lipids, hormones, cholesterol, calcium ions, etc. that are bound to an albumin polypeptide.

By "treated scrum albumin" is meant scrum albumin that is treated to reduce, remove, replace or otherwise inactivate the associated-molecule-component of the serum albumin, for example, human serum albumin that is incubated at an elevated temperature, human serum albumin that is contacted with sodium octanoate or human serum albumin that, is contacted with a porous material.

By "ion-exchange resin" is meant a material that when contacted with a solution containing ions, replaces one or more of the ions with one or more different ions, for example, a material that replaces one or more calcium ions with one or more sodium ions.

By "germ cell" is meant a sperm cell or an egg cell.

By "pluripotent stem cell" is meant a cell that can differentiate into cells of all three germ layers (endoderm, mesoderm, and ectoderm) in vivo.

By "somatic cell" is meant a cell that is not a pluripotent stem cell or a germ cell, for example, a skin cell.

By "glucose-responsive insulin-producing cell" is meant a cell that, when exposed to a certain concentration of glucose, produces and/or secretes an amount of insulin that is different from (either less than or more than) the amount of insulin produced and/or secreted by the cell when the cell is exposed to a different concentration of glucose, for example, a β-cell.

By "hematopoietic cell" is meant a blood cell or a cell that can differentiate into a blood cell, for example, a hematopoietic stem cell or a white blood cell.

By "cardiac cell" is meant a heart cell or a cell that can differentiate into a heart cell, for example, a cardiac stem cell or a cardiomyocyte.

By "retinal cell" is meant a cell of the retina or a cell that can differentiate into a cell of the retina, for example, a retinal pigmented epithelial cell.

By "skin cell" is meant a cell that is normally found in the skin, for example, a fibroblast, a keratinocyte, a melanocyte, an adipocyte, a mesenchymal stem cell, an adipose stem cell or a blood cell.

By "Wnt signaling agonist" is meant a molecule that performs one or more of the biological functions of one or more members of the Wnt family of proteins, for example, Wnt1, Wnt2, Wnt3, Wnt3a or 2-amino-4-[3,4-(methylenedioxy)benzylamino]-6-(3-methoxyphenyl)pyrimidime.

By "IL-6 signaling agonist" is meant a molecule that performs one or more of the biological functions of IL-6 protein, for example, IL-6 protein or IL-6 receptor (also known as soluble IL-6 receptor, IL-6R, IL-6R alpha, etc.).

By "TGF-β signaling agonist" is meant a molecule that performs one or more of the biological functions of one or more members of the TGF-β superfamily of proteins, for example, TGF-β1, TGF-β3, Activin A, BMP-4 or Nodal.

Serum albumin is a common component of serum-free cell-culture media. It has now been discovered that serum albumin can inhibit transfection, and that including untreated serum albumin in a transfection medium at concentrations normally used in serum-free cell-culture media can result in low transfection efficiency and/or low cell viability during transfection (see Examples). The serum albumin polypeptide binds to a wide variety of molecules, including lipids, ions, cholesterol, etc., both in vitro and in vivo, and as a result, both serum albumin that is isolated from blood and recombinant serum albumin comprise a polypeptide component and an associated-molecule component. It has now been discovered that the low transfection efficiency and low cell viability during transfection caused by serum albumin are caused in part by the associated-molecule component of the serum albumin. It has been further discovered that transfection efficiency can be dramatically increased and transfection-associated toxicity can be dramatically reduced by partially or completely reducing, removing, replacing or otherwise inactivating the associated-molecule component of serum albumin. Certain embodiments of the invention, are therefore directed to a method for treating a protein to partially or completely reduce, remove, replace or otherwise inactivate the associated-molecule component of the protein. Other embodiments are directed to a protein that is treated to partially or completely reduce, remove, replace or otherwise inactivate the associated-molecule component of the protein.

Certain embodiments are directed to methods for treating a protein by contacting the protein with one or more molecules that reduce the low transfection efficiency and/or low cell viability during transfection caused by the protein. Serum albumin has several binding sites that can bind lipids. Contacting serum albumin with the short-chain fatty acid, sodium octanoate (also known as "octanoic acid", "octanoate", "caprylate" or "caprylic acid") was found to reduce the low transfection efficiency and low cell viability during transfection caused by serum albumin (see Examples). Other substances that can be used to treat a protein include: capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, docosahexaenoic acid, tryptophan, N-acetyl tryptophan, cholesterol, other fatty acids, and salts, mixtures, fragments, and derivatives thereof. Substances for treating a protein can be pure substances, well-defined mixtures or complex or undefined mixtures such as animal-based or plant-based oils, for example, cod-liver oil. In certain embodiments, a protein is treated after the protein is purified. In other embodiments, a protein is treated before the protein is purified. In still other embodiments, a protein is treated at the same time that the protein is purified. In still other embodiments, a protein is treated, and the protein is not purified.

Incubating a protein at an elevated temperature can cause partial or complete denaturation of the polypeptide component of the protein, which can reduce or eliminate binding sites that are critical to maintaining the associated-molecule component of the protein. Certain embodiments are therefore directed to methods for treating a protein by incubating the protein at an elevated temperature. In one embodiment, the protein is incubated at a temperature of at least 40 C. for at least 10 minutes. In another embodiment, the protein is incubated at a temperature of at least 55 C. for feast 30 minutes. In a preferred embodiment, the protein is contacted with sodium octanoate, and then incubated at 60 C. for several hours, preferably between 1 hour and 24 hours, more preferably between 2 hours and 6 hours. In a more preferred embodiment, the concentration of sodium octanoate is between 5 mM and 50 mM, more preferably between 10 mM and 40 mM. In certain embodiments, the sodium octanoate is replaced with or used in combination with at least one element of the group comprising: capric acid, laurte acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, docosahexaenoic acid, tryptophan, N-acetyl tryptophan, and cholesterol or a salt, mixture, fragment, and derivative thereof.

Glycation and glycosylation are processes by which one or more sugar molecules are bound to a protein. Glycation and glycosylation can impact the binding properties of a protein, and serum albumin contains several potential glycation sites. Certain embodiments are therefore directed to methods for treating a protein by glycating or glycosylating the protein.

Ion-exchange resins, including an ion-exchange, cation-exchange, and mixed-bed resins, are routinely used to deionize solutions. The associated-molecule component of proteins such as scrum albumin often comprises ions. Certain embodiments are therefore directed to a method for treating a protein by contacting the protein with one or more ion-exchange resins. In a preferred embodiment, the one or more ion-exchange resins includes a mixed-bed resin containing functional groups with proton (H+) and hydroxyl (OH−) forms. In another preferred embodiment, the one or more ion-exchange resins includes an indicator that changes color as the resin becomes saturated with ions, it is recognized that, in addition to contacting with one or more ion-exchange resins, other methods can be used to reduce, remove, replace or otherwise inactivate the associated-molecule component of a protein, including contacting the protein with charcoal, which may be activated and/or treated with a chemical such as dextran sulfate, dialysis (including dilution resulting in de-association of the associated-molecule component, whether or not the de-associated molecules are subsequently removed from the solution), crystallization, chromatography, electrophoresis, heat treatment, low-temperature treatment, high-pH treatment, low-pH treatment, organic-solvent precipitation, and affinity purification.

Certain methods for treating a protein preferentially reduce, remove, replace or otherwise inactivate specific types of molecules, in certain situations, it is therefore beneficial to combine two or more methods for treating a protein to reduce the low transfection efficiency and/or low cell viability during transfection caused by the protein. Certain embodiments are therefore directed to a method for treating a protein using two or more methods to reduce, remove, replace or otherwise inactivate the associated-molecule component of the protein. In a preferred embodiment, a protein is contacted with one or more ion-exchange resins, and with activated charcoal. In another preferred embodiment, a protein is contacted with sodium octanoate, incubated at an elevated temperature, contacted with one or more ion-exchange resins, and contacted with activated charcoal. In a more preferred embodiment, the protein is serum albumin, and the elevated temperature is at least 50 C.

Certain elements of the associated-molecule component of a protein can be beneficial to cells in culture, and/or to transfection, for example, certain resolvins, protecting lipoxins, maresins, eicosanoids, prostacyclins, thromboxanes, leukotrienes, cyclopentenone prostaglandins, and glucocorticoids. Certain embodiments are therefore directed to a method for treating a protein to reduce, remove, replace or otherwise inactivate the associated-molecule component of the protein without reducing, removing, replacing or otherwise inactivating one or more beneficial elements of the associated-molecule component of the protein. Other embodiments are directed to a method for treating a protein to reduce, remove, replace or otherwise inactivate the associated-molecule component of the protein, and further contacting the protein with one or more molecules comprising one or more beneficial elements of the associated-molecule component of the protein. Still other embodiments are directed to a method for treating a protein to reduce the low transfection efficiency and/or low cell viability during transfection caused by the protein by contacting the protein with one or more molecules comprising one or more beneficial elements of the associated-molecule component of the protein. Still other embodiments are directed to a method for increasing transfection efficiency and/or increasing cell viability during transfection by contacting a cell with one or more molecules comprising one or more beneficial elements of the associated-molecule component of a protein. In a preferred embodiment, the protein is contacted with one or more ion-exchange resins or charcoal, and is further contacted with a glucocorticoid, preferably cortisol, prednisone, prednisolone, methylprednisolone, dexamethasone or betamethasone. In another preferred embodiment, the cell is contacted with a glucocorticoid, preferably cortisol, prednisone, prednisolone, methylprednisolone, dexamethasone or betamethasone. In a more preferred embodiment, the cell is transfected, preferably with one or more synthetic RNA molecules.

Other embodiments are directed to a medium containing a protein that is treated according to the methods of the present invention. In a preferred embodiment, the medium is a transfection medium. In a more preferred embodiment, the medium also supports efficient transfection and high cell viability. In certain embodiments, the protein and one or more molecules that reduce the low transfection efficiency and/or low cell viability during transfection caused by the protein are added independently to the medium. In a preferred embodiment, the protein is treated before being mixed with one or more of the other ingredients of the medium. It has now been discovered that, under certain conditions, the concentration of fatty acids/lipids that is commonly used in serum-tree cell-culture media is insufficient to treat the large amount of serum albumin that is commonly used in these media. Certain embodiments are therefore directed to a medium that contains a ratio of fatty acids/lipids to protein that is sufficient to treat the protein. In a preferred embodiment, the medium contains a standard amount of fatty acids/lipids, and a reduced amount of protein, preferably between 0.01 g/L and 2 g/L, more preferably between 0.05 g/L and 0.5 g/L. Certain embodiments are directed to a medium containing a protein that is treated by contacting the protein with one or more ion-exchange resins. In a preferred embodiment, the protein is treated by contacting the protein with the one or more ion-exchange resins before the protein is added to the medium. In a more preferred embodiment, the medium is a transfection medium and the degree of treatment is adjusted to control the efficiency of transaction and/or cell viability, preferably to allow transfections at least every 48 hours, more preferably to allow transfections every 24 hours, more preferably to allow transfection reagent-nucleic acid complexes to be left in contact with cells for about 24 hours. Leaving the transfection reagent-nucleic acid complexes in contact with cells for an extended period of time may be desirable in part because doing so can reduce handling and media consumption, especially in a multi-transfection protocol. In a preferred embodiment, the medium is prepared by first treating a concentrated solution of serum albumin by contacting the concentrated solution of serum albumin with one or more ion-exchange resins, then removing the one or more ion-exchange resins from the concentrated solution of serum albumin, and finally adding the treated concentrated solution of serum albumin to the other components of the medium. In a more preferred embodiment, the concentrated solution of serum albumin is further contacted with activated charcoal before adding the concentrated solution of serum albumin to the other components of the medium. In an even more preferred embodiment, the concentrated solution of serum albumin is first contacted with sodium octanoate, then raised to a temperature of at least 50 C. for at least 10 minutes, then contacted with one or more ion-exchange resins, then contacted with activated charcoal, then added to the other components of the medium.

In certain situations, it is desirable to replace animal-derived components with non-animal-derived and/or recombinant components in part because non-animal-derived and/or recombinant components can be produced with a higher degree of consistency than animal-derived components, and in part because non-animal-derived and/or recombinant components carry less risk of contamination with toxic and/or pathogenic substances than do animal-derived components. Certain embodiments are therefore directed to a protein that is non-animal-derived and/or recombinant. Other embodiments are directed to a medium, wherein some or all of the components of the medium are non-animal-derived and/or recombinant. In a preferred embodiment, the protein is recombinant serum albumin. In another preferred embodiment, the protein is recombinant human serum albumin. In a more preferred embodiment, the protein is recombinant serum albumin and all of the components of the medium are non-animal-derived and/or recombinant.

The N-terminus of serum albumin contains a nickel- and copper-binding domain, which is an important antigenic determinant. Deleting the aspartic acid residue from the N-terminus of serum albumin eliminates the nickel- and copper-binding activity of serum albumin, and results in a hypoallergenic variant of the protein. Certain embodiments are therefore directed to a protein that has modified binding characteristics and/or other desirable characteristics such as hypoallergenicity. In a preferred embodiment, the protein is serum albumin, and the serum albumin lacks the N-terminal aspartic acid of serum albumin.

Other embodiments are directed to methods for transfecting a cell using the medium of the present invention. In a preferred embodiment, a cell is transfected with one or more nucleic acids, and the transfection is performed using a transfection reagent, more preferably a lipid-based transfection reagent. In a more preferred embodiment, the one or more nucleic acids includes at least one RNA molecule. In another preferred embodiment, the cell is transfected with one or more nucleic acids, and the one or more nucleic acids encodes at least one element of the group comprising: p53, Tert, a cytokine, a secreted protein, a membrane-bound protein, an enzyme, a chromatin-modifying protein, a DNA-binding protein, a histone deacetylase, a pathogen-associated molecular pattern, and a tumor-associated antigen or a biologically active fragment, analogue, variant or family-member thereof. In another preferred embodiment, the cell is transfected repeatedly, preferably at least 2 times during 10 consecutive days, more preferably at least 3 times during 7 consecutive days, even more preferably at least 4 times during 6 consecutive days.

Reprogramming can be performed by transfecting cells with one or more nucleic acids encoding one or more reprogramming factors, and culturing the cells in a medium that supports the reprogrammed cells. Examples of reprogramming factors include, but are not limited to: Oct4 protein, Sox2 protein, Klf4 protein, c-Myc protein, 1-Myc protein, Tert protein, Nanog protein, Lin28 protein, Utf1 protein, Aicda protein, miR200 micro-RNA, miR302 micro-RNA, miR367 micro-RNA, miR369 micro-RNA and biologically active fragments, analogues, variants and family-members thereof. It has now been discovered that the efficiency, speed, and reliability of reprogramming can be enhanced by using a medium that supports both the cells and the reprogrammed cells. Certain embodiments are therefore directed to a medium that supports the growth of multiple cell types. In a preferred embodiment, the medium supports the growth of human fibroblasts and human pluripotent stem cells. It has now been further discovered that the efficiency, speed, and reliability of reprogramming can be dramatically enhanced by transfecting cells according to the methods of the present invention (see Examples). Certain embodiments are therefore directed to methods for reprogramming a cell by transfecting the cell according to the methods of the present invention. In a preferred embodiment, the cell is transfected with one or more nucleic acids. In a more preferred embodiment, the one or more nucleic acids includes RNA molecules encoding Oct4 protein. In an even more preferred embodiment, the one or more nucleic acids includes RNA molecules encoding Oct4, Sox2, Klf4, and c-Myc proteins. In a still more preferred embodiment, the one or more nucleic acids also includes RNA molecules encoding Lin28 protein. In another even more preferred embodiment, the RNA molecules also comprise at least one pseudouridine or 5-methylcytidine residue. In a still more preferred embodiment, at least 20% of the uridine and cytidine residues of the RNA molecules are replaced with pseudouridine and 5-methylcytidine residues, respectively. In a still more preferred embodiment, about 100% of the uridine and cytidine residues of the RNA molecules are replaced with pseudouridine and 5-methylcytidine residues, respectively. In one embodiment, the cell is a human skin cell, and the human skin cell is reprogrammed to a pluripotent stem cell. In another embodiment, the cell is a human skin cell, and the human skin cell is reprogrammed to a glucose-responsive insulin-producing cell. Examples of other cells that can be reprogrammed according to the methods of the present invention and other cells to which a cell can be reprogrammed according to the methods of the present invention include, but are not limited to: skin cells, pluripotent stem cells, mesenchymal stem cells, P-cells, retinal pigmented epithelial cells, hematopoietic cells, cardiac cells, airway epithelial cells, neural stem cells, neurons, glial cells, bone cells, blood cells, and dental pulp stem cells.

Importantly, infecting skin cells with viruses encoding Oct4, Sox2, Klf4, and c-Myc, combined with culturing the cells in a medium that supports the growth of cardiomyocytes, has been shown to cause reprogramming of the skin cells to cardiomyocytes, without first reprogramming the skin cells to pluripotent stem cells[16]. In certain situations, for example when generating a personalized therapeutic, direct reprogramming (reprogramming one somatic cell to another somatic cell without first reprogramming the somatic cell to a pluripotent stem cell, also known as "transdifferentiation") may be desirable, in part because culturing pluripotent stem cells can be time-consuming and expensive, the additional handling involved in establishing and characterizing a stable pluripotent stem cell line carries an increased risk of contamination, and the additional time in culture associated with first producing pluripotent stem cells carries an increased risk of genomic instability and the acquisition of mutations, including point mutations, copy-number variations, and karyotypic abnormalities. Certain embodiments are therefore directed to methods for reprogramming a somatic cell, wherein the cell is reprogrammed to a somatic cell, and wherein a characterized pluripotent stem-cell line is not produced. In a preferred embodiment, the somatic cell is contacted with one or more RNA molecules that encodes at least one protein selected from the group comprising: Oct4, Sox2, Klf4, c-Myc, Nanog, Lm28, Utf1, and Aicda. In another preferred embodiment, the somatic cell is reprogrammed to a somatic cell selected from the group comprising: a skin cell, a mesenchymal stem cell, a β-cell, a retinal pigmented epithelial cell, a hematopoietic cell, a cardiac cell, an airway epithelial cell, a neural stem cell, a neuron, a glial cell, a bone cell, a blood cell, and a dental pulp stem cell.

All previously reported methods for reprogramming cells by transfecting them with RNA encoding reprogramming factors require the use of feeders. In many situations, the use of feeders is not desirable in part because feeders are generally derived from animal or allogeneic sources, and thus carry risks of immunogetricity and contamination with pathogens. It has now been discovered that the medium of the present invention can enable RNA reprogramming without feeders (see Examples). It has been further discovered that reprogramming cells according to the methods of the present invention, wherein the cells are not contacted with feeders, can be rapid, efficient, and reliable. Certain embodiments are therefore directed to methods for reprogramming a cell, wherein the cell is not contacted with feeders. In a preferred embodiment, the cell is transfected with one or more RNA molecules encoding one or more reprogramming factors.

It has been further discovered that the starting cell density can correlate with reprogramming efficiency when cells are reprogrammed according to the methods of the present invention. Certain embodiments are therefore directed to methods for reprogramming cells, wherein the cells are plated at a density of between 100 cells/cm$^2$ and 100,000 cells/cm$^2$. In a preferred embodiment, the cells are plated at a density of between 2000 cells/cm$^2$ and 20,000 cells/cm$^2$.

It has been further discovered that, in certain situations, fewer total transfections are required to reprogram a cell according to the methods of the present invention than according to other methods (see Examples), Certain embodiments are therefore directed to methods for reprogramming a cell, wherein between 2 and 12 transfections are performed during 20 consecutive days. In a preferred embodiment, between 4 and 10 transfections are performed during 15 consecutive days. In a more preferred embodiment, between 4 and 8 transfections are performed during 10 consecutive days. It is recognized that when nucleic acids are added to a medium in which a cell is cultured, the cell may likely come into contact with and/or internalize more than one nucleic acid either simultaneously or at different times. A cell can therefore be contacted with a nucleic acid more than once, i.e. repeatedly, even when nucleic acids are added only once to a medium in which the cell is cultured.

When cells are transfected and are cultured in the presence of feeders, the feeders are, in general, also transfected with the nucleic acid. It has now been discovered that feeders can prevent excessive transfection of cells in part by removing excess transfection reagent-nucleic acid complexes from the medium. It has been further discovered that the efficiency, speed, and reliability of reprogramming without feeders can be increased when the excess transfection reagent-nucleic acid complexes are rinsed off of the cells after transfection. Certain embodiments are therefore directed to methods for transfecting a cell without using feeders, wherein the cell is rinsed after transfection. It is recognized that the rinsing can be performed using, for example, cell-culture medium, transfection medium, basal medium, or a simple solution such as phosphate-buffered saline. In a preferred embodiment, the transfection is repeated, and the cell is rinsed after each transfection. In a more preferred embodiment, the transfection is repeated, the cell is rinsed after each transfection, and the cell is reprogrammed.

Feeders can promote adhesion of cells to a surface by secreting molecules such as collagen that bind to the surface ("cell-adhesion molecules"). Proteins, including integrins, on the surface of cells can bind to these molecules, and cause the cells to adhere to the surface. It has now been discovered that cells can be reprogrammed without feeders by coating a surface with one or more cell-adhesion molecules, and that fibronectin and vitronectin are particularly suited for this purpose (see Examples). Certain embodiments are therefore directed to methods for transfecting and/or reprogramming a cell, wherein the cell is contacted with a surface that is contacted with one or more cell-adhesion molecules. In a preferred embodiment, the one or more cell-adhesion molecules includes at least one element of the group comprising: poly-L-lysine, poly-L-ornithine, RGD peptide, fibronectin, vitronectin, collagen, and laminin or a biologically active fragment, analogue, variant or family-member thereof. In another preferred embodiment the one or more cell-adhesion molecules is fibronectin or a biologically active fragment thereof. In yet another preferred embodiment, the fibronectin is recombinant. In a more preferred embodiment, the one or more cell-adhesion molecules is a mixture of fibronectin and vitronectin or biologically active fragments thereof. In an even more preferred embodiment, both the fibronectin and vitronectin are recombinant. It is recognized that the contacting of the surface with the one or more cell-adhesion molecules can be performed separately, and/or by mixing the one or more cell-adhesion molecules with the medium.

Of note, nucleic acids can contain one or more non-canonical, or "modified", residues (a residue other than adenine, guanine, thymine, uracil, and cytosine or the standard nucleoside, nucleotide, deoxynucleoside or deoxynucleotide derivatives thereof). Of particular note, pseudouridine-triphosphate can be substituted for uridine-triphosphate in an in vitro-transcription reaction to yield synthetic RNA, wherein up to 100% of the uridine residues of the synthetic RNA are replaced with pseudouridine residues[17-21]. In vitro-transcription yields RNA with residual immunogenicity[12, 13, 22], even when pseudouridine and 5-methylcytidine are completely substituted for uridine and cytidine, respectively[15]. For this reason, it is common to add an immunosuppressant to the transfection medium when transfecting cells with RNA. In certain situations, adding an immunosuppressant to the transfection medium is not desirable in part because the recombinant immunosuppressant most commonly used for this purpose, B18R, is expensive and difficult to manufacture. It has now been discovered that cells can be reprogrammed according to the methods of the present invention, without using B18R or any other immunosuppressant (see Examples). It has been further discovered that reprogramming cells according to the methods of the present invention without using immunosuppressants can be rapid, efficient, and reliable (see Examples). Certain embodiments are therefore directed to methods for reprogramming a cell, wherein the transfection medium does not contain an immunosuppressant. In certain situations, such as when using a high cell density, it is beneficial to add an immunosuppressant to the medium of the present invention. Certain embodiments are therefore directed to methods for reprogramming, wherein the medium contains an immunosuppressant such as B18R or dexamethasone. In a preferred embodiment, cells are plated at less than 20,000 cells/cm$^2$, and the transfection medium does not contain an immunosuppressant.

It has now been discovered that when an immunosuppressant is not used, reprogramming efficiency, speed, and reliability can be increased by reducing the nucleic-acid dose (see Examples), increasing the time between transections, performing multiple media changes to remove secreted inflammatory cytokines from the medium, and/or performing one or more rinsing steps to remove excess transfection reagent-nucleic acid complexes and/or inflammatory cytokines from the cells. Certain embodiments are therefore directed to methods for reprogramming a cell, wherein the transfection medium does not contain an immunosuppressant, and wherein the nucleic-acid dose is chosen to prevent excessive toxicity. In a preferred embodiment, the nucleic-acid dose is less than 2 µg/well of a 6-well plate, preferably between 0.25 µg/well of a 6-well plate and 1 µg/well of a 6-well plate. Other embodiments are directed to methods for reprogramming a cell, wherein the transfection medium does not contain an immunosuppressant, and wherein at least 2 transfections are performed, and the time between 2 transfections is at least 36 hours. In a preferred embodiment, at least 5 transfections are performed, and the time between each transfection is 48 hours. Other embodiments are directed to methods for reprogramming a cell, wherein the transfection medium does not contain an immunosuppressant, and wherein at least 2 media changes are performed between transfections. Other embodiments are directed to methods for reprogramming cells, wherein the transfection medium does not contain an immunosuppressant, and wherein the cells are rinsed after each transfection. In a preferred embodiment, the cells are rinsed with basal medium. In a more preferred embodiment, the cells are rinsed with transfection medium.

It has now been discovered that, in certain situations, certain specific morphological changes, such as the formation of high-phase regions in the cellular cytoplasm and clear, circular areas resembling the lipid-containing vesicles of adipocytes, are observed in cells that are transfected according to the methods of the present invention. Examples of these morphological changes are shown in the figures of the accompanying drawings. It has been discovered that these morphological changes can be predictive of transfection efficiency, toxicity, and reprogramming efficiency. Certain embodiments are therefore directed to methods for developing a transfection protocol based on the morphological changes observed in cells after transfection with a nucleic acid. Other embodiments are directed to methods for developing a reprogramming protocol based on the morphological changes observed in cells after transfection with a nucleic acid.

Reprogrammed cells produced according to certain preferred embodiments of the present invention are suitable in particular for therapeutic applications including transplantation into patients, as they do not contain exogenous DNA sequences, and they are not exposed to animal-derived or human-derived products, which are undefined, and which may contain toxic and/or pathogenic contaminants. Furthermore, the high speed, efficiency, and reliability of the methods of the present invention reduce the risk of acquisition and accumulation of mutations and other chromosomal abnormalities. Certain embodiments of the present invention can thus be used to generate cells that have a safety profile that supports their use in therapeutic applications. For example, reprogramming cells using RNA and the medium of the present invention, wherein the medium does not contain animal or human-derived components, can yield cells that have not been exposed to allogeneic material. Certain embodiments are therefore directed to a reprogrammed cell that has a desirable safety profile. In a preferred embodiment, the reprogrammed cell has a normal karyotype and fewer than 100 single nucleotide variants in coding regions relative to the patient genome, more preferably fewer than 50 single nucleotide variants in coding regions relative to the patient genome, more preferably fewer than 10 single nucleotide variants in coding regions relative to the patient genome.

Certain embodiments are directed to a kit containing one or more materials needed to practice the present invention. In a preferred embodiment, the kit contains the present invention and a solution containing RNA encoding one or more reprogramming factors. In another preferred embodiment, the kit further contains a transfection reagent. In yet another preferred embodiment, the kit contains aliquots of the medium of the present invention, wherein each aliquot contains transfection reagent-nucleic acid, complexes that are stabilized either by chemical treatment or by freezing.

Endotoxins and nucleases can co-purify and/or become associated with other proteins, such as serum albumin. Recombinant proteins, in particular, often have high levels of associated endotoxins and nucleases, due in part to the lysis of cells that can take place during their production. Endotoxins and nucleases can be reduced, removed, replaced or otherwise inactivated by many of the methods of the present invention, including, for example, by acetylation, by addition of a stabilizer such as sodium octanoate, followed by heat treatment, by the addition of nuclease inhibitors to the albumin solution and/or medium, by crystallization, by contacting with one or more ion-exchange resins, by contacting with charcoal, by preparative electrophoresis or by affinity chromatography. It has now been discovered that partially or completely reducing, removing, replacing of otherwise inactivating endotoxins and/or nucleases from a medium and/or from one or more components of a medium can increase the efficiency with which cells can be transfected with nucleic acids, and the efficiency with which cells can be reprogrammed. Certain embodiments are therefore directed to a method for transfecting a cell with one or more nucleic acids, wherein the transfection medium is treated to partially or completely reduce, remove, replace or otherwise inactivate one or more endotoxins and/or nucleases. In a preferred embodiment, the medium contains serum albumin, preferably recombinant serum albumin. In a more preferred embodiment, the serum albumin is contacted with sodium octanoate, and the serum albumin is incubated at an elevated temperature, preferably at least 50 C. for at least 10 minutes. In an even more preferred embodiment, the serum albumin is further contacted with one or more ion-exchange resins and/or charcoal. Other embodiments are directed to a medium that causes minimal degradation of nucleic acids. In a preferred embodiment, the medium contains less than 1 EU/mL, preferably less than 0.1 EU/mL, more preferably less than 0.01 EU/mL. In another preferred embodiment, the cell-culture medium supports reprogramming.

It is recognized that protein-based lipid earners such as serum albumin can be replaced with non-protein-based lipid carriers such as methyl-beta-cyclodextrin. It is also recognized that the medium of the present invention can be used without a lipid carrier, wherein transfection is performed using a method that does not require the presence of a lipid carrier, for example, using one or more polymer-based transfection reagents or peptide-based transfection reagents.

It is further recognized that many protein-associated molecules, such as metals, can be highly toxic to cells. This toxicity can cause decreased viability in culture, as well as the acquisition of mutations. Certain embodiments of the present invention thus have the additional benefit of producing cells that are free from toxic molecules.

The associated-molecule component of a protein can be measured by suspending the protein in solution and measuring the conductivity of the solution. Certain embodiments are therefore directed to a medium that contains a protein, wherein a 10% solution of the protein in water has a conductivity of less than 500 μmho/cm. In a preferred embodiment, the solution has a conductivity of less than 50 μmho/cm.

A low-oxygen environment can be beneficial for the culture of many types of cells. Certain embodiments are therefore directed to methods for culturing, transfecting and/or reprogramming cells according to the methods of the present invention, wherein the cells are cultured, transfected, and/or reprogrammed in a low-oxygen environment. In a preferred embodiment, the cells are cultured, transfected, and/or reprogrammed in an environment containing between 2% and 10% oxygen. In a more preferred embodiment, the cells are cultured, transfected, and/or reprogrammed in an environment containing between 4% and 6% oxygen.

The amount of nucleic acid delivered to cells can be increased to increase the desired effect of the nucleic acid. However, increasing the amount of nucleic acid delivered to cells beyond a certain point causes a decrease in the viability of the cells, due in part to toxicity of the transfection reagent. It has now been discovered that when a nucleic acid is delivered to a population of cells in a fixed volume (for example, cells in a region of tissue or cells grown in a cell-culture vessel), the amount of nucleic acid delivered to each cell depends on the total amount of nucleic acid delivered to the population of cells and to the density of the cells, with a higher cell density resulting in less nucleic acid being delivered to each cell. In certain embodiments of the present invention, a cell is transfected with one or more nucleic acids more than once. Under certain conditions, for example when the cells are proliferating, the cell density may change from one transfection to the next. Certain embodiments are Therefore directed to methods for transfecting a cell with a nucleic acid, wherein the cell is transfected more than once, and wherein the amount of nucleic acid delivered to the cell is different for two subsequent transfections. In a preferred embodiment, the cell proliferates between two of the transfections, and the amount of nucleic acid delivered to the cell is greater for the second of the two transfections than for the first of the two transfections. In another preferred embodiment, the cell is transfected more than twice, and the amount of nucleic acid delivered to the cell is greater for the second of three transfections than for the first of the same three transfections, and the amount of nucleic acid delivered to the cells is greater for the third of the same three transfections than for the second of the same three transfections. In yet another preferred embodiment, the cell is transfected more than once, and the maximum amount of nucleic acid delivered to the cell during each transfection is sufficiently low to yield at least 80% viability (i.e. at least 80% of the cells survive each transfection) for at least two consecutive transfections.

It has now been farther discovered that modulating the amount of nucleic acid delivered to a population of proliferating cells in a series of transfections can result in both an increased effect of the nucleic acid and increased viability of the cells. It has also now been discovered that in certain situations, when cells are contacted with one or more nucleic acids encoding one or more reprogramming factors in a series of transfections, the efficiency of reprogramming is increased when the amount of nucleic acid delivered in later transfections is greater than the amount of nucleic acid delivered in earlier transfections, for at least part of the series of transfections. Certain embodiments are therefore directed to a method for reprogramming a cell, wherein one or more nucleic acids is repeatedly delivered to the cell in a series of transfections, and the amount of the nucleic acid delivered to the cell is greater for at least one later transfection than for at least, one earlier transfection. In a preferred embodiment, the cell is transfected between 2 and 10 times, preferably between 3 and 8 times, more preferably between 4 and 6 times. In another preferred embodiment, the one or more nucleic acids Includes at least one RNA molecule, the cell is transfected between 2 and 10 times, and the amount of nucleic acid delivered to the cell in each transfection is the same as or greater than the amount of nucleic acid delivered to the cell in the most recent previous transfection. In yet another preferred embodiment, the amount of nucleic acid delivered to the cell in the first transfection is between 20 ng/cm$^2$ and 250 ng/cm$^2$. In yet another preferred embodiment, the amount of nucleic acid delivered to the cell in the last transfection is between 100 ng/cm$^2$ and 600 ng/cm$^2$. In yet another preferred embodiment, the cell is transfected 5 times at intervals of between 12 and 48 hours, and the amount of nucleic acid delivered to the cell is 25 ng/cm$^2$ for the first transfection, 50 ng/cm$^2$ for the second transfection, 100 ng/cm$^2$ for the third transfection, 200 ng/cm$^2$ for the fourth transfection, and 400 ng/cm$^2$ for the fifth transfection.

In certain situations, the performance of a medium can be improved by conditioning the medium. It has now been discovered that the transfection efficiency and viability of cells cultured in the medium of the present invention can be improved by conditioning the medium. Certain embodiments are therefore directed to a method for conditioning a medium. Other embodiments are directed to a medium that is conditioned. In a preferred embodiment, the feeders are fibroblasts, and the medium is conditioned for approximately 24 hours. Other embodiments are directed to a method for transfecting a cell, wherein the transfection medium is conditioned. Other embodiments are directed to a method for reprogramming a cell, wherein the medium is conditioned. In a preferred embodiment, the feeders are mitotically inactivated, for example, by exposure to a chemical such as mitomycin-C or by exposure to gamma radiation. In certain situations, it is beneficial to use only autologous materials, in part to avoid the risk of disease transmission front the feeders to the cell being reprogrammed. Certain embodiments are therefore directed to a method for transfecting a cell, wherein the transfection medium is conditioned, and wherein the feeders are derived from the same individual as the cell being transfected. Other embodiments are directed to a method for reprogramming a cell, wherein the medium is conditioned, and wherein the feeders are derived from the same individual as the cell being reprogrammed.

Several molecules are added to media by conditioning. Certain embodiments are therefore directed to a medium that is supplemented with one or more molecules that are present its a conditioned medium. In a preferred embodiment, the medium is supplemented with Wnt1, Wnt2, Wnt3, Wnt3a or a biologically active fragment, analogue, variant, agonist, or family-member thereof. In another preferred embodiment, the medium is supplemented with TGF-β or a biologically active fragment, analogue, variant, agonist, or family-member thereof. In yet another preferred embodiment, a cell is reprogrammed according to the method of the present invention, wherein the medium is not supplemented with TGF-β for between 1 and 5 days, and is then supplemented with TGF-β for at least 2 days. In yet another preferred embodiment, the medium is supplemented with IL-6, IL-6R or a biologically active fragment, analogue, variant, agonist, or family-member thereof. In yet another preferred embodiment, the medium is supplemented with a sphingolipid or a fatty acid. In yet another preferred embodiment, the sphingolipid is lysophosphatidic acid, lysosphingomyelin, sphingosine-1-phosphate or a biologically active analogue, variant or derivative thereof.

In addition to mitotically inactivating cells, under certain conditions, irradiation can change the gene expression of cells, causing cells to produce less of certain proteins and more of certain other proteins that non-irradiated cells, for example, members of the Wnt family of proteins[23, 24]. In addition, certain members of the Wnt family of proteins promote the growth and transformation of cells[25, 26]. It has now been discovered that, in certain situations, the efficiency of RNA reprogramming can be greatly increased by contacting the cell with a medium that is conditioned using irradiated feeders instead of mitomycin-c-treated feeders. It has been further discovered that the increase in reprogramming efficiency observed when using irradiated feeders is caused in part by Wnt proteins that are secreted by the feeders. Certain embodiments are therefore directed to a method for reprogramming a cell, wherein the cell is contacted with Wnt1, Wnt2, Wnt3, Wnt3a or a biologically active fragment, analogue, variant, family-member or agonist thereof, including agonists of downstream targets of Wnt proteins, and/or agents that mimic one or more of the biological effects of Wnt proteins, for example, 2-amino-4-[3,4-(methylenedioxy)benzylamino]-6-(3-methoxyphenyl) pyrimidine[27]. In a preferred embodiment, the cell is further contacted with one or more RNA molecules. In a more preferred embodiment, at least 2 transfections are performed during 5 consecutive days. In another preferred embodiment, the cell is a human skin cell. In yet another preferred embodiment, the one or more RNA molecules encodes the proteins Oct4, Sox2, Klf4, and c-Myc.

It is recognized that the medium of the present invention can be used to maintain cells, including fibroblasts and human pluripotent stem cells, in culture (i.e. as a "maintenance medium"; see Examples). Certain embodiments are therefore directed to the medium of the present invention, wherein the medium is used as a maintenance medium. In a preferred embodiment, the medium does not contain any human-derived components. In a more preferred embodiment, the medium is chemically defined. It is also recognized that the addition of components that are known to promote the growth of certain cell types, for example lipid-rich albumin, which can promote the growth of pluripotent stem cells[4], can be added to the medium of the present invention to promote the growth of these cell types when the medium is used as a transfection medium, as a maintenance medium, or as both a transfection medium and a maintenance medium.

DNA-based reprogramming methods generally use cells that are derived from established cultures of primary cells, such as fibroblasts. Because of the low efficiency of these methods, DNA-based reprogramming is difficult or impossible to use with cells derived from patient samples, which generally contain too few cells to produce a sufficient number of reprogrammed cells using these methods. In contrast, the high efficiency of certain embodiments of the present invention allows reliable reprogramming from small numbers of cells, including from single cells. Certain embodiments of the present invention can thus be used to reprogram cells from a biopsy sample, without first establishing a large culture (see Examples). Reprogramming cells directly from a biopsy is desirable in certain situations, especially when generating a personalized therapeutic, in part because establishing a large culture of primary cells is time-consuming, the additional handling involved in establishing a large culture carries an increased risk of contamination, and the additional time in culture carries an increased risk of genomic instability and the acquisition of mutations, including, point mutations, copy-number variations, and karyotypic abnormalities. Certain embodiments are therefore directed to methods for reprogramming a cell by harvesting the cell from a patient or from a biopsy sample, and reprogramming the cell according to the methods of the present invention. In a preferred embodiment, the cell is reprogrammed without first establishing a large culture (i.e. a first transfection is performed before the culture is passaged more than twice). In another preferred embodiment, the cell is harvested from a patient, and a first transfection is performed after no more than 14 days from the time the cell is first plated. In yet another preferred embodiment, the cell is harvested from a biopsy sample, and a first transfection is performed after no more than 7 days from the time the cell is first plated. In yet another preferred embodiment, the biopsy is a full-thickness dermal punch biopsy, the cell is harvested from the biopsy sample by treatment with one or more enzymes, the cell is plated on a surface that is coated with a cell-adhesion molecule and/or the cell is plated in a medium that contains a cell-adhesion molecule, the cell is transfected with one or more nucleic acids comprising at least one RNA molecule, and a first transfection is performed after no more than 14 days from the time the cell is first plated. In yet another preferred embodiment, the cell is harvested from blood. In yet another preferred embodiment, the cell is plated in a medium containing one or more proteins that is derived from the patient's blood. In yet another preferred embodiment, the cell is plated in DMEM/F12+2 mM L-alanyl-L-glutamine+between 5% and 25% patient-derived serum, more preferably between about 10% and about 20% patient-derived serum, most preferably about 20% patient-derived serum.

It has now been discovered that cells, including fibroblasts, can be efficiently isolated from tissue by placing the tissue in a container, and suspending the tissue at the air-liquid interface of a solution containing an enzyme that digests one or more protein components of the tissue, such that the cells that are freed from the tissue fall to the bottom of the container, where they can then be collected. This method is advantageous, in part because it enables isolation and collection of cells from a tissue without mechanical disruption of the tissue, which can damage cells and create a large amount of debris. It has now been further discovered that the lipophilic nature of the epidermis facilitates suspension of skin tissue at an air-liquid interface, and that fibroblasts are efficiently isolated from tissue obtained by a full-thickness skin punch biopsy using this method. Certain embodiments are therefore directed to a method for isolating cells from a tissue sample by suspending the tissue sample at an air-liquid interface, wherein the liquid contains an enzyme that digests one or more protein components of the tissue. In a preferred embodiment, the tissue sample is a full-thickness skin punch biopsy sample. In another preferred embodiment, the enzyme is collagenase. In a more preferred embodiment, the collagenase is animal-component free. In yet another preferred embodiment, the collagenase is present at a concentration of between 0.1 mg/mL and 10 mg/mL, more preferably between 0.5 mg/mL and 5 mg/mL. In yet another preferred embodiment, the tissue is suspended for between 1 h and 24 h, more preferably between 6 h and 12 h. This method is also advantageous as a method for isolating cells for reprogramming, in part because it can yield a well-dissociated cell suspension without the need for harsh mechanical disruption, and because it can eliminate the need for establishing a stable culture before transfection.

It has now been further discovered that, in certain situations, transfecting cells with a mixture of RNA encoding Oct4, Sox2, Klf4, and c-Myc using the medium of the present invention causes the rate of proliferation of the cells to increase. When the amount of RNA delivered to the cells is too low to ensure that all of the cells are transfected, only a fraction of the cells may show an increased proliferation rate. In certain situations, such as when generating a personalized therapeutic, increasing the proliferation rate of cells may be desirable, in part because doing so can reduce the time necessary to generate the therapeutic, and therefore can reduce the cost of the therapeutic. Certain embodiments are therefore directed to transfecting a cell with a mixture of RNA encoding Oct4, Sox2, Klf4, and c-Myc using the medium of the present invention, wherein the cell shows an increased proliferation rate. In a preferred embodiment, the cell is harvested from a biopsy sample, and the cell is transfected between 2 and 7 times. In another preferred embodiment, cells showing an increased proliferation rate are isolated from the culture. In yet another preferred embodiment, cells showing an increased proliferation rate are expanded and cultured in a medium that supports the growth of one or more cell types, and are reprogrammed to a cell of one of the one or more cell types.

Certain embodiments are directed to therapeutics comprising one or more cells that are transfected and/or reprogrammed according to the methods of the present invention. In a preferred embodiment, a cell is transfected and/or reprogrammed, and the transfected and/or reprogrammed cell is introduced to a patient. In another preferred embodiment, the cell is harvested from the same patient to whom the transfected and/or reprogrammed cell is introduced. Examples of diseases that can be treated with therapeutics of the present invention include, but are not limited to: Alzheimer's disease, spinal cord injury, amyotrophic lateral sclerosis, cystic fibrosis, heart disease, including ischemic and dilated cardiomyopathy, macular degeneration, Parkinson's disease, Huntington's disease, diabetes, sickle-cell anemia, thalassemia, Fanconi anemia, xeroderma pigmentosum, muscular dystrophy, severe combined immunodeficiency, hereditary sensory neuropathy, and HIV/AIDS. In certain embodiments, the therapeutic comprises a cosmetic. In a preferred embodiment, a cell is harvested from a patient, the cell is reprogrammed and expanded to a large number of adipose cells, thus producing a cosmetic, and the cosmetic is introduced to the patient. In a more preferred embodiment, the cosmetic is further used for tissue reconstruction.

While detailed examples are provided herein for the production of specific types of cells and for the production of therapeutics comprising specific types of cells, it is recognized that the methods of the present invention can be used to produce many other types of cells, and to produce therapeutics comprising one or more of many other types of cells, for example, by reprogramming a cell according to the methods of the present invention, and culturing the cell under conditions that mimic one or more aspects of development by providing conditions that resemble the conditions present in the cellular microenvironment during development.

Certain embodiments are directed to libraries of therapeutics comprising cells with a variety of human leukocyte antigen (HLA) types ("HLA-matched libraries"). An HLA-matched library is beneficial in part because it provides for the rapid production and/or distribution of therapeutics without the patient having to wait for a therapeutic to be produced from the patient's cells. Such a library is particularly beneficial for the treatment of heart disease and diseases of the blood and/or immune system for which patients may benefit from the immediate availability of a therapeutic.

Certain embodiments are directed to cells that are used as tissue/organ models and/or disease models. In one embodiment, a skin cell is reprogrammed and expanded to a large number of cardiac cells, and the cardiac cells are used for screening bioactive molecules for cardiotoxicity (i.e. safety testing). In another embodiment, a skin cell from a patient with Alzheimer's disease is reprogrammed and expanded to a large number of cortical neurons, and the cortical neurons are used for screening bioactive molecules for reducing the accumulation of insoluble plaques (i.e. efficacy testing). Certain embodiments of the present invention are therefore useful for safety testing and/or efficacy testing.

Certain embodiments are directed to a method for encapsulating cells and/or seeding cells in a scaffold, and to cells that are encapsulated and/or cells that are seeded in a scaffold. In certain situations, encapsulating cells is beneficial in part because encapsulated cells can be less immunogenic than non-encapsulated cells. In a preferred embodiment, a cell is reprogrammed to a glucose-responsive insulin-producing cell, the glucose-responsive insulin-producing cell is encapsulated in a material such as alginate, and the encapsulated glucose-responsive insulin-producing cell is introduced into a patient with type 1 diabetes. In another preferred embodiment, the introducing is by intraperitoneal injection or intraportal injection. In certain situations, seeding cells in a scaffold is beneficial in part because a scaffold can provide mechanical stability. In a preferred embodiment, a cell is reprogrammed and expanded into a large number of fibroblasts and keratinocytes, the fibroblasts and keratinocytes are seeded in a scaffold comprising collagen, and the seeded scaffold is applied to a wound, forming a synthetic skin graft. In another preferred embodiment, a cell is reprogrammed, the reprogrammed cell is mixed with a scaffold in liquid or slurry form, the mixture is introduced into the patient, and the stiffness of the scaffold increases upon or after introduction.

Certain embodiments are directed to a method for purifying the cells of the present invention. Reprogramming often produces populations of cells including cells with the desired phenotype and cells with one or more undesired phenotypes. Certain embodiments are therefore directed to a method for purifying reprogrammed cells. In a preferred embodiment, the cells are purified using a density gradient. In another preferred embodiment, the cells are purified by contacting the cells with one or more antibodies that allows the separation of cells having one or more desired phenotypes from cells having one or more undesired phenotypes. In a more preferred embodiment, the antibody is bound to a substrate, preferably a magnetic bead. In another more preferred embodiment, the antibody is bound to a fluorescent molecule, and the separation is performed by fluorescence activated cell sorting (FACS) or other similar means. In another preferred embodiment, cells with an undesired phenotype are prevented from proliferating, preferably by contacting the cells with one or more molecules that prevents the cells from dividing, preferably mitomycin-c, 5-aza-deoxycytidine, fluorouracil or a biologically active analogue or derivative thereof. Other embodiments are directed to a therapeutic comprising cells that are purified to enrich the fraction of cells having one or more desired phenotypes.

Certain embodiments are directed to a method for producing animal models, including models of mutations and diseases. In one embodiment, an animal skin cell is reprogrammed to a pluripotent stem cell according to the methods of the present invention. In another embodiment, 1-100 reprogrammed cells are injected into a blastocyst, and the blastocyst is implanted into the uterine horn of an animal. In a preferred embodiment, the animal is selected from the group comprising: a cat, a dog, a mouse, a pig, a primate, and a rat.

The present invention therefore has the aim of providing products for both research and therapeutic use.

EXAMPLES

Example 1 Synthesis of Reprogramming RNA

Figure 1:
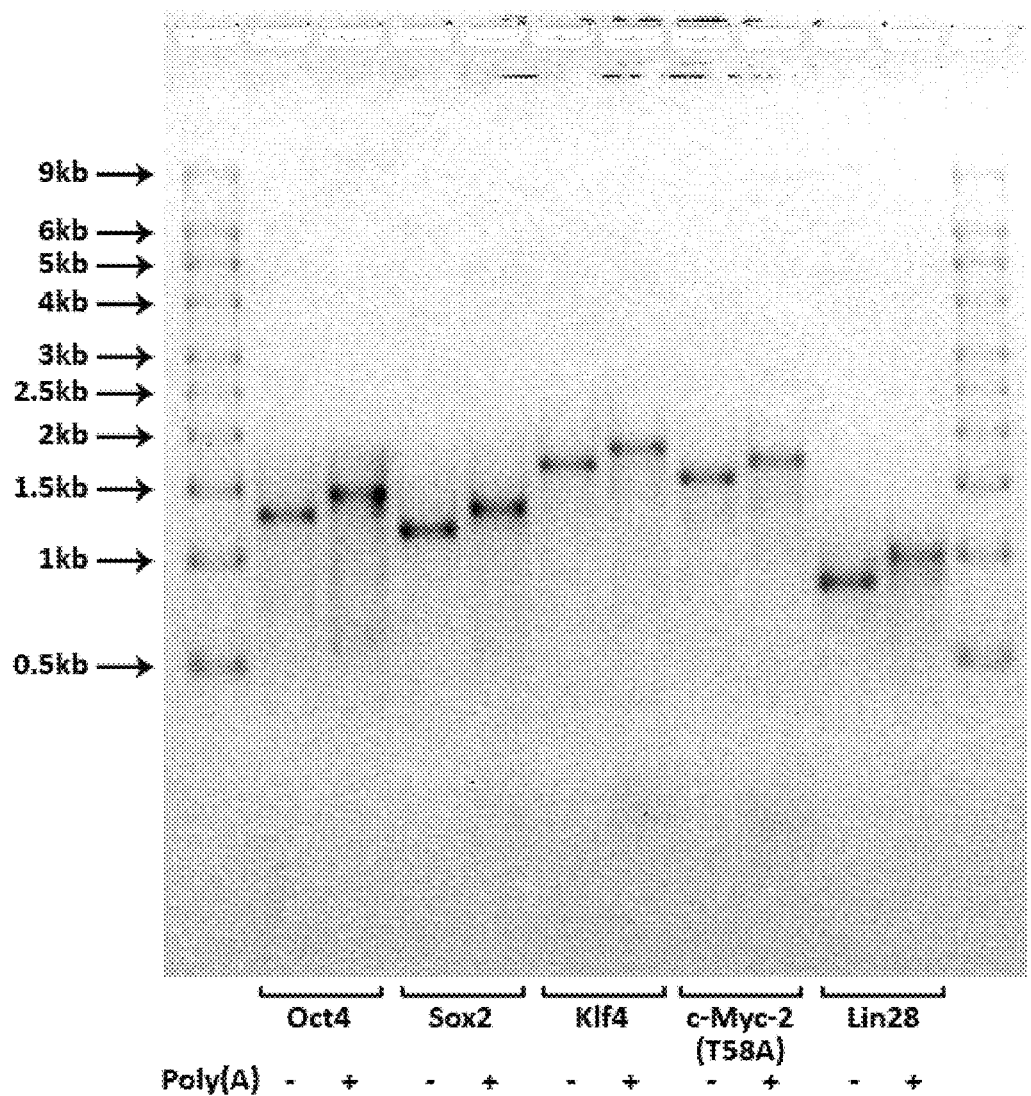
FIG. 1 depicts RNA encoding the indicated proteins, resolved on a denaturing formaldehyde-agarose gel.

RNA encoding the human proteins Oct4, Sox2, Klf4, c-Myc-2 (T58A), and Lin28 and comprising adenosine, guanosine, pseudouridine, and 5-methylcytidine residues[17-20], was synthesized from DNA templates using the T7 High Yield RNA Synthesis Kit (New England Biolabs, Inc.), according to the manufacturer's instructions. The resulting RNA was analyzed by agarose gel electrophoresis to assess the quality of the RNA (FIG. 1). The RNA was then diluted to 200 ng/μL, and an RNase inhibitor (Superase-In™, Life Technologies Corporation) was added at a concentration of 1 μL/100 μg of RNA. RNA solutions were stored at 4 C. indefinitely. RNA encoding Oct4, Sox2, Klf4, c-Myc-2 (T58A), and Lin28 was mixed at a molar ratio of 3:1:1:1:1.

Example 2 Transfection of Cells with Reprogramming RNA 2 ug RNA and 6 μL transfection reagent (Lipofectamine™ RNAiMAX, Life Technologies Corporation) were first diluted separately in complexation medium (Opts-MEM®, Life Technologies Corporation) to a total volume of 60 μL each. Diluted RNA and transfection reagent were then mixed and incubated for 15 min at room temperature, according to the transfection reagent-manufacturer's instructions. Complexes were then added to cells in culture. Between 60 μL and 120 μL of complexes were added to each well of a 6-well plate, which already contained 2 mL of transfection medium per well. Plates were then shaken gently to distribute the complexes throughout the well. Cells were incubated with complexes for 2 hours to overnight, before replacing the medium with fresh transfection medium (2 mL/well).

Figure 2:
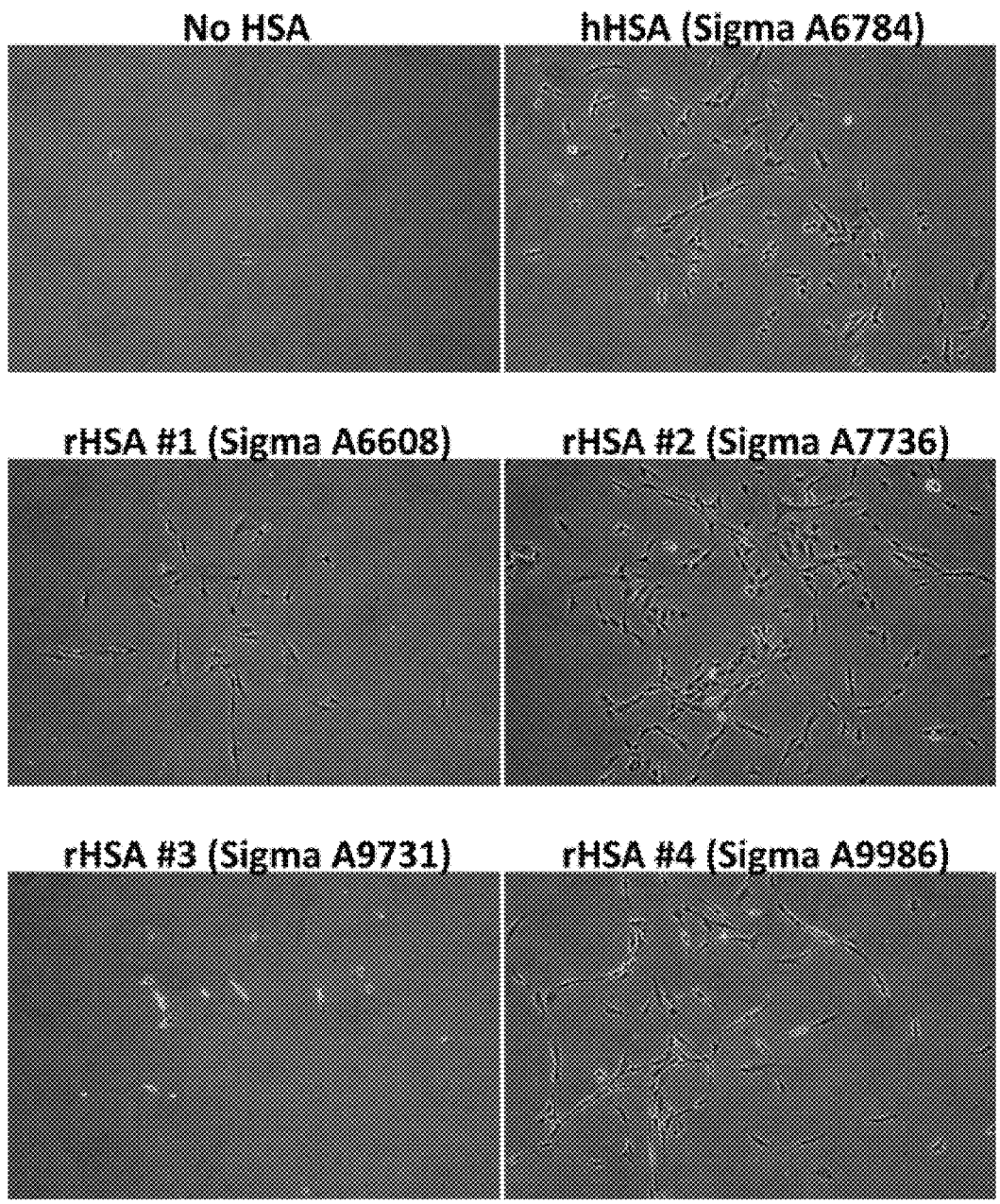
FIG. 2 depicts primary human fibroblasts cultured in media containing the indicated HSA. The cells were transfected once with a mixture of RNA encoding Oct4, Sox2, Klf4, c-Myc-2 (T58A), and Lin28 two days before the pictures were taken.

Example 3 Analysis of the Ability of Untreated Human Serum Albumin Preparations to Support Nucleic Acid Transfection and RNA Reprogramming Primary human neonatal fibroblasts were cultured in medium with or without 5 mg/mL HSA. Cohn Fraction V (A6784, Sigma-Aldrich Co. LLC.), and four different recombinant HSA preparations (A6608, A7736, A9731, and A9986, all from Sigma-Aldrich Co. LLC.) were screened. Cells were transfected according to Example 2, with RNA synthesized according to Example 1. While untransfected cells grew well in media containing any of the HSA preparations, in transfected wells, each of the HSA preparations yielded dramatically different cell morphologies and cell densities, and none resulted in morphological changes indicative of reprogramming (FIG. 2).

Example 4 Production of Octanoate-Treated Human Serum Albumin

A 10% solution of HSA was pre-Incubated with 22 mM sodium chloride and 16 mM sodium octanoate (Sigma-Aldrich Co. LLC), and was incubated at 37 C. for 3 hours before assembly of the complete medium.

Example 5 Analysis of Transfection Efficiency and Viability of Cells Cultured in Media Containing Octanoate-Treated Human Serum Albumin Primary human neonatal fibroblasts were cultured in media containing recombinant HSA treated according to Example 4 or containing treated blood-derived HSA (Bio-Pure HSA, Biological Industries). Cells were transfected daily, according to Example 2, with RNA synthesized according to Example 1, beginning on day 0. Pictures were taken on day 3. Several small areas of cells undergoing morphological changes resembling mesenchymal to epithelial transition, were observed in the wells containing octanoate, indicating an increased transfection efficiency (FIG. 3, second row, arrows). Many large areas of morphological changes resembling mesenchymal to epithelial transition were observed in the samples containing the treated blood-derived HSA (FIG. 3, fourth row, arrows). In both cases, the morphological changes were characteristic of reprogramming.

Example 6 Reprogramming Human Fibroblasts Using Media Containing Octanoate-Treated Human Serum Albumin Primary human neonatal fibroblasts were plated in 6-well plates at a density of 5000 cells/well in fibroblast medium (DMEM+10% fetal bovine serum). After 6 hours, the medium was replaced with transfection medium containing octanoate-treated HSA. The cells were transfected daily, according to Example 2, with RNA synthesized according to Example 1, beginning on day 0. By day 5, the well contained several areas of cells exhibiting morphology consistent with reprogramming. This experiment did not include the use of feeders or immunosuppressants.

Example 7 Treatment of Human Serum Albumin Using Ion-Exchange Chromatography

A 20% solution of recombinant HSA produced in *Pichia pastoris* (A7736, Sigma-Aldrich Co. LLC.) was prepared by dissolving 2 g of HSA in 10 mL of nuclease-free water with gentle agitation at room temperature. The HSA solution was then deionized by first adding 1 g of mixed-bed deionizing resin (AG 501-XS(D), Bio-Rad Laboratories, Inc.), and rocking for 1 h at room temperature. The HSA solution was then decanted into a tube containing 5 g of fresh resin, and was rocked for 4 h at room temperature. Finally, the deionized HSA solution was decanted, adjusted to a 10% total protein content with nuclease-free water, filter-sterilized using a 0.2 μm PES-membrane filter, and stored at 4 C.

Example 8 Transfection Medium Formulation

A cell-culture medium was developed to support efficient transfection of cells with nucleic acids and efficient reprogramming:

DMEM/F12+10 μg/mL insulin+5.5 μg/mL transferrin+ 6.7 ng/mL sodium selenite+20 ng/mL bFGF+5 mg/mL treated human serum albumin.

Variants of this medium were also developed to provide improved performance when used with specific transfection reagents, specific nucleic acids, and specific cell types:

DMEM/F12+10 μg/mL insulin+5.5 μg/mL transferrin+ 6.7 ng/mL sodium selenite+4.5 μg/mL cholesterol+20 ng/mL bFGF+5 mg/mL treated human serum albumin, DMEM/F12+10 μg/mL insulin+5.5 μg/mL transferrin+ 6.7 ng/mL sodium selenite+10 μg/mL fatty acids+20 μg/mL bFGF+5 mg/mL treated human serum albumin, DMEM/F12+10 μg/mL insulin+5.5 μg/mL transferrin+ 6.7 ng/mL sodium selenite+4.5 μg/mL cholesterol+10 μg/mL fatty acids+20 ng/mL bFGF+5 mg/mL treated human serum albumin, DMEM/F12+15 mM HEPES+10 μg/mL insulin+5.3 μg/mL transferrin+6.7 ng/mL sodium selenite+4.5 μg/mL cholesterol+10 g/mL fatty acids+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+4.5 μg/mL cholesterol 10 μg/mL fatty acids+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium, selenite+4.5 μg/mL cholesterol+10 μg/mL cod liver oil fatty acids (methyl esters)+25 μg/mL polyoxyethylenesorbitan monooleate+2 μg/mL D-alpha-tocopherol acetate+1 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolanune+10 μg/mL cod liver oil fatty acids (methyl esters)+25 μg/mL polyoxyethylenesorbitan monooleate+2 μg/mL D-alpha-tocopherol acetate+1 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+25 μg/mL polyoxyethylenesorbitan monooleate+2 μg/mL D-alpha-tocopherol acetate+1 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+10 μg/mL cod liver oil fatty acids (methyl esters)+2 μg/mL D-alpha-tocopherol acetate+10 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine 4.5 μg/mL cholesterol+10 μg/mL cod liver oil fatty acids (methyl esters)+25 μg/mL polyoxyethylenesorbitan monooleate+1 μg/mL L-ascorbic acid 2-phosphate sesquimagnesium salt hydrate+ 0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+10 μg/mL cod liver oil fatty acids (methyl esters)+25 μg/mL polyoxyethylenesorbitan monooleate+2 μg/mL D-alpha-tocopherol acetate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+10 μg/mL cod liver oil fatty acids (methyl esters)+25 μg/mL polyoxyethylenesorbitan monooleate+2 μg/mL D-alpha-tocopherol acetate+1 μg/mL L-ascorbic acid 2-phosphate sesquimagnesium salt hydrate+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+10 μg/mL, cod liver oil fatty acids (methyl esters)+25 μg/mL polyoxyethylenesorbitan monooleate+2 μg/mL D-alpha-tocopherol acetate+1 μg/mL L-ascorbic acid 2-phosphate sesquimagnesium salt hydrate+0.1% PLURONIC F-68 (poloxamer 188)+20 μg/mL bFGF+5 mg/mL treated human serum albumin*, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+0.5 μg/mL alpha-linolenic acid+0.5 μg/mL gamma-linolenic acid+0.5 μg/mL dihomo-gamma-linoleic acid+0.5 μg/mL octadecatetraenoic acid+0.5 μg/mL eicosapentaenoic acid+0.5 μg/mL docosahexaenoic acid+0.5 μg/mL arachidonic acid+0.5 μg/mL myristic acid+1.85 μg/mL palmitic acid+2.5 μg/mL stearic acid+0.25 μg/mL palmitoleic acid+ 25 μg/mL polyoxyethylenesorbitan monooleate+2 μg/mL D-alpha-tocopherol acetate+1.85 μg/mL oleic acid+0.65 μg/mL linoleic acid+1 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+0.5 ng/mL gamma-linolenic acid+0.5 μg/mL dihomo-gamma-linolenic acid+0.5 μg/mL octadecatetraenoic acid+ 0.5 μg/mL eicosapentaenoic acid+0.5 μg/mL docosahexaenoic acid+0.5 μg/mL arachidonic acid+0.5 μg/mL myristic acid+1.85 μg/mL palmitic acid+2.5 μg/mL stearic acid+0.25 μg/mL palmitoleic acid+25 μg/mL polyoxyethylenesorbitan monooleate+2 μg/mL D-alpha-tocopherol acetate+1.85 μg/mL oleic acid+0.65 μg/mL linoleic acid+1 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 μg/mL insulin+5.5 μg/mL transferrin+6.7 ng/mL sodium selenite+2 μg/mL ethanolamine+4.5 μg/mL cholesterol+0.5 μg/mL alpha-linolenic acid+0.5 μg/mL dihomo-gamma-linolenic acid+0.5 μg/mL octadecatetraenoic acid+ 0.5 μg/mL eicosapentaenoic acid+0.5 μg/mL docosahexaenoic acid+0.5 μg/mL arachidonic acid+0.5 μg/mL myristic acid+1.85 μg/mL palmitic acid+2.5 μg/mL stearic acid+0.25 μg/mL palmitoleic acid+25 μg/mL polyoxyethylenesorbitan monooleate+2 μg/mL D-alpha-tocopherol acetate+1.85 μg/mL oleic acid+0.65 μg/mL linoleic acid+1 μg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 ng/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL eicosapentaenoic acid+0.5 µg/mL docosahexaenoic acid+0.5 µg/mL, arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 g/mL octadecatetraenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+

0.5 µg/mL octadecatetraenoic acid+0.5 µg/mL eicosapentaenoic acid+0.5 µg/mL docosahexaenoic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/ml dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin 6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/ml alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+25 µg/mL polyoxyethylenesorbitan monooleate+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 g/ml, insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 ng/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/ml, palmitoleic acid+25 µg/mL polyoxyethylenesorbitan monooleate+2 µg/mL D-alpha-tocopherol acetate+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/ml, myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate 1.85 µg/mL oleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+0.5 µg/mL alpha-linolenic acid+0.5 µg/ml gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+0.65 µg/mL linoleic acid+1 µg/ml L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+2 µg/mL D-alpha-tocopherol acetate+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+1.85 µg/mL oleic acid+0.65 µg/mL linoleic acid+1 µg/mL L-ascorbic acid 2-phosphate sesquimagnesium salt hydrate+0.1 PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+1.85 µg/mL oleic acid+0.65 µg/mL linoleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 ng/mL stearic acid+0.25 µg/mL palmitoleic acid+25 µg/mL polyoxyethylenesorbitan monooleate+2 µg/mL D-alpha-tocopherol acetate+1.85 µg/mL oleic acid+1 µg/mL L-ascorbic acid 2-phosphate sesquimagnesium salt hydrate+0.1% PLURONIC F-68 (poloxamer 188)+20 ng/mL bFGF+5 mg/mL treated human scram albumin, DMEM/F12+5 mM HEPES+2 mM L-alanyl-L-glutamine+10 µg/mL insulin+5.5 µg/mL transferrin+6.7 ng/mL sodium selenite+2 µg/mL ethanolamine+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin 6.7 µg/mL sodium selenite+2 µg/mL ethanolamine+0.5 µg/mL octadecatetraenoic acid+0.5 µg/mL eicosapentaenoic acid+0.5 µg/mL docosahexaenoic acid+0.5 µg/mL arachidonic acid+

0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+1 µg/mL L-ascorbic acid 2-phosphate sesquimagnesium salt, hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+0.5 µg/mL octadecatetraenoic acid+0.5 µg/mL eicosapentaenoic acid+0.5 µg/mL docosahexaenoic acid+0.5 µg/mL arachidonic acid 0.5 µg/mL myristic acid+1.85 µg/mL palmitic acid+2.5 µg/mL stearic acid+0.25 µg/mL palmitoleic acid+1.85 µg/mL oleic acid+1 µg/mL L-ascorbic acid 2-phosphate sesquimagnesium salt hydrate+0.1% PLURONIC F-68 (poloxamer 188)+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.85 µg/mL palmitic acid+2.5 µg/mL stearic acid+0.25 µg/mL palmitoleic acid+25 µg/mL polyoxyethylenesorbitan monooleate+2 µg/mL D-alpha-tocopherol acetate+1.85 µg/mL oleic acid+1 µg/mL linoleic acid 1 µg/mL L-ascorbic acid 2-phosphate sesquimagnesium salt hydrate+20 ng/mL bFGF+5 mg/mL treated human serum albumin, DMEM/F12+15 mM HEPES+2 mM L-alanyl-L-glutamine+10 µg/mL insulin+5.5 µg/mL transferrin+6.7 ng/mL sodium selenite+2 µg/mL ethanolamine+4.5 µg/mL cholesterol+0.5 µg/mL alpha-linolenic acid+0.5 µg/mL gamma-linolenic acid+0.5 µg/mL dihomo-gamma-linolenic acid+0.5 µg/mL octadecatetraenoic acid+0.5 µg/mL eicosapentaenoic acid+0.5 µg/mL docosahexaenoic acid+0.5 µg/mL arachidonic acid+0.5 µg/mL myristic acid+1.5 µg/mL palmitic acid+2.5 µg/mL stearic acid+0.25 µg/mL palmitoleic acid+25 µg/mL, polyoxyethylenesorbitan monooleate+2 µg/mL D-alpha-tocopherol acetate+1.85 µg/mL oleic acid+1 µg/mL L-ascorbic acid 2-phosphate sesquimagnesium salt hydrate+20 ng/mL bFGF+5 mg/mL treated human serum albumin.

This variant, in which the treated human serum albumin was treated by addition of 32 mM sodium octanoate, followed by heating at 60 C. for 4 h, followed by treatment with ion-exchange resin (AG501-X8(D)) for 6 h at room temperature, followed by treatment with dextran-coated activated charcoal (C6241, Sigma-Aldrich Co, LLC.) overnight at room temperature, followed by centrifugation, filtering, adjustment to a 10% solution with nuclease-free water, followed by addition to the other components of the medium, which was then conditioned for 24 h on irradiated human neonatal fibroblast feeders, was used as the transfection medium in Examples 2-7 and Examples 9-12, unless otherwise noted, and cells were plated on fibronectin-coated plates, unless otherwise noted. It is recognized that the formulation of the transfection medium can be adjusted to meet the needs of the specific cell types being cultured. It is further recognized that treated human serum albumin can be replaced with other treated albumin, for example, treated bovine serum albumin, without negatively affecting the performance of the medium. It is further recognized that other glutamine sources can be used instead of or in addition to L-alanyl-L-glutamine, for example, L-glutamine, that other buffering systems can be used instead of or in addition to HEPES, for example, phosphate, bicarbonate, etc., that selenium can be provided in other forms Instead of or in addition, to sodium selenite, for example, selenous acid, that other antioxidants can be used instead of or in addition to L-ascorbic acid 2-phosphate sesquimagnesium salt hydrate and/or D-alpha-tocopherol acetate, for example, L-ascorbic acid, that other surfactants can be used instead of or in addition to polyoxyethylenesorbitan monooleate and/or PLURONIC F-68 (poloxamer 188), for example, PLURONIC F-127 (poloxamer 407), that other basal media can be used instead of or in addition to DMEM/F12, for example, MEM, DMEM, etc., and that the components of the culture medium can be varied with time, for example, by using a medium without TGF-β from day 0 to day 5, and then using a medium containing 2 ng/mL TGF-β after day 5, without negatively affecting the performance of the medium. It is further recognized that other ingredients can be added, for example, fatty acids, lysophosphatidic acid, lysosphingomyelin, sphingosine-1-phosphate, other sphingolipids, members of the TGF-β/NODAL family of proteins, IL-6, members of the Wnt family of proteins, etc., at appropriate concentrations, without negatively affecting the performance of the medium, and that ingredients that are known to promote or inhibit the growth of specific cell types and/or agonists and/or antagonists of proteins or other molecules that are known to promote or inhibit the growth of specific cell types can be added to the medium at appropriate concentrations when it is used with those cell types without negatively affecting the performance of the medium, for example, sphingosine-1-phosphate and pluripotent stem cells. The present invention relates equally to ingredients that are added as purified compounds, to ingredients that are added as parts of well-defined mixtures, to ingredients that are added as parts of complex or undefined mixtures, for example, animal or plant oils, and to ingredients that are added by biological processes, for example, conditioning. The concentrations of the components can be varied from the listed values within ranges that will be obvious to persons skilled in the art without negatively affecting the performance of the medium.

Example 9 Analysis of Transfection Efficiency and Viability of Cells Cultured in Media Containing Ion-Exchange-Resin-Treated Human Serum Albumin Primary human neonatal fibroblasts were transfected according to Example 2, using RNA synthesized according to Example 1, beginning on day 0. Pictures were taken on day 2 (FIG. 4). Cells in the well containing untreated HSA (middle panel of FIG. 4) exhibited low viability compared to either the well containing treated blood-derived HSA or ion-exchange-resin-treated recombinant HSA.

Example 10 Reprogramming Human Fibroblasts Using Ion-Exchange-Resin-Treated Human Serum Albumin Primary human neonatal fibroblasts were plated in 6-well plates on feeders at a density of 10,000 cells/well in fibroblast medium (DMEM 4-10% fetal bovine serum). The cells were transfected according to Example 2, using RNA synthesized according to Example 1, beginning on day 0. A passage with a split ratio of 1:20 was performed on day 4. Pictures were taken on day 10. The well contained many large colonies of cells exhibiting morphology consistent with reprogramming (FIG. 5). No colonies were observed in wells exposed to cell-culture media containing untreated HSA.

Example 11 Reprogramming Human Fibroblasts Without Using Feeders or Immunosuppressants Primary human fibroblasts were plated in 6-well plates at a density of 20,000 cells/well in fibroblast medium (DMEM+10% fetal bovine serum), After 6 hours, the medium was replaced with transfection medium containing treated HSA and not containing immunosuppressants, and the cells were transfected as in Example 10, except that the dose of RNA was reduced to 1 µg/well and the total number of transfections was reduced to 5. Pictures were taken on day 7 (FIG. 6). Small colonies of cells exhibiting morphology consistent with reprogramming became visible as early as day 5. On day 7, the medium was replaced with DMEM/F12+20% Knockout™ Serum Replacement (Life Technologies Corporation)+1× non-essential amino acids+2 mM L-glutamine, conditioned on irradiated mouse embryonic fibroblasts for 24 hours, and then supplemented with 20 ng/mL bFGF and 10 µM Y-27632. Large colonies with a reprogrammed morphology became visible as early as day 8. Colonies were picked on day 10, and plated in wells coated with basement membrane extract (Cultrex® Human BME Pathclear®, Trevigen Inc.) (FIG. 7). Cells grew rapidly, and were passaged to establish lines. Established lines stained positive for the pluripotent stem-cell markers Oct4 and SSEA4 (FIG. 8). The entire protocol was repeated, and similar results were obtained (FIG. 9).

Example 12 Efficient, Rapid Derivation and Reprogramming of Cells from Human Skin Biopsy Tissue A full-thickness dermal punch biopsy was performed on a healthy, 31 year-old volunteer, according to an approved protocol. Briefly, an area of skin on the left, upper arm was anesthetized by topical application of 2.5% lidocaine. The field was disinfected with 70% isopropanol, and a full-thickness dermal biopsy was performed using a 1.5 mm-diameter punch (FIG. 10A). The tissue was rinsed in phosphate-buffered saline (PBS), and was placed in a 1.5 mL tube containing 250 µL of TrypLE™ Select CTS™ (Life Technologies Corporation), and incubated at 37 C. for 30 min. The tissue was then transferred to a 1.5 mL tube containing 250 µL of DMEM/F12-CTS™ (Life Technologies Corporation)+5 mg/mL collagenase, and incubated at 37 C. for 2 h (FIG. 10B). The epidermis was removed using forceps, and the tissue was mechanically dissociated. Cells were rinsed twice in DMEM/F12-CTS™ and were plated in fibronectin-coated wells of 24-well and 96-well plates. Phlebotomy was also performed on the same volunteer, and venous blood was collected in Vacutainer® SST™ tubes (Becton, Dickinson and Company). Serum was isolated according to the manufacturer's protocol. Isogenic plating medium was prepared by mixing DMEM/F12-CTS™+2 mM L-alanyl-L-glutamine (Sigma-Aldrich Co. LLC.)+20% human serum. Cells from the dermal tissue sample were plated either in transfection medium or in isogenic plating medium. After 2 days, the wells were rinsed, and the medium was replaced with transfection medium. Many cells with a fibroblast morphology attached and began to spread by day 2 (FIG. 10C). Cells were transfected according to Example 2, using RNA synthesized according to Example 1, beginning on day 2, with all volumes scaled to accommodate the smaller wells. By day 5, areas of cells with morphologies consistent with reprogramming were observed (FIG. 11).

Example 13 Diabetes Disease Models for Screening Bioactive Molecules

Cells are reprogrammed according to Example 11 or Example 12, and are then cultured in DMEM/F12+0.2% HSA+0.5×N2 supplement+0.5×B27 supplement+100 ng/mL activin A+1 µM wortmannin for 4 days, followed by 1:1 F12/IMDM+0.5% HSA+0.5% ITS supplement+0.5× B27 supplement+2 µM retinoic acid+20 ng/mL FGF7+50 ng/mL NOGGIN for 4 days, followed by DMEM+0.5% HSA+1% ITS supplement+1×N2 supplement+50 ng/mL EGF for 5 days, followed by DMEM/F12+1% ITS supplement+10 ng/mL bFGF+10 mM nicotinamide+50 ng/mL exendin-4+10 ng/mL BMP4 for 7-9 days to generate glucose-responsive insulin-producing cells. Alternatively, cells are reprogrammed according to Example 11 or Example 12, and are then cultured in 1:1 F12/IMDM+0.5% HSA+0.5% ITS supplement+0.5×B27 supplement+2 µM retinoic acid+ 20 ng/mL FGF7+50 ng/mL NOGGIN for 4 days, followed by DMEM+0.5% HSA+1% ITS supplement+1×N2 supplement+50 ng/mL EGF for 5 days, followed by DMEM/F12+ 1% ITS supplement+10 ng/mL bFGF+10 mM nicotinamide+50 ng/mL exendin-4+10 ng/mL BMP4 for 7-9 days to generate glucose-responsive insulin-producing cells, without generating definitive endoderm cells. Alternatively, cells are reprogrammed according to Example 11 or Example 12, and are then cultured in 1:1 F12/IMDM+0.5% HSA+0.5% ITS supplement+0.5×1327 supplement+2 µM retinoic acid+ 20 ng/mL FGF7+50 ng/mL NOGGIN for 4 days, followed by DMEM/F12+1% ITS supplement+10 ng/mL bFGF+10 mM nicotinamide+50 ng/mL exendin-4+10 ng/mL BMP4 for 7-9 days to generate glucose-responsive insulin-producing cells, without generating definitive endoderm cells, and without expanding progenitor cells. While endodermal cells or insulin-producing cells can be isolated, from other cells present in the culture, this method generates a sufficiently high percentage of glucose-responsive insulin producing cells that such isolation is not generally required. The resulting cells can then be used in vitro or in vivo for screening bioactive molecules for the study of diabetes or for the development of therapeutics for diabetes.

Example 14 Personalized Cell-Replacement Therapy for Type 1 Diabetes Comprising Reprogrammed Cells Patient skin cells are reprogrammed to glucose-responsive insulin-producing cells according to Example 12 and Example 13. Cells are then enzymatically released from the culture vessel, and between about $1\times10^6$ and about $1\times10^7$ cells are injected into the intraperitoneal space or into the portal vein. In the case of intraperitoneal injection, cells are pre-mixed with an extracellular matrix protein to prevent excessive migration. Cells engraft and begin producing insulin, Insulin/C-peptide levels are monitored, and additional injections are performed as necessary.

Example 15 Cardiac Disease Models for Screening Bioactive Molecules

Cells were reprogrammed according to Example 11, and were then cultured in DMEM/F12+0.2% HSA+0.5×N2 supplement+0.5×B2.7 supplement+100 ng/mL activin A+1 µM wortmannin for 4 days, followed by 1:1 F12/IMDM+ 0.5% HSA+0.5% ITS supplement+0.5×B27 supplement+2 µM retinoic acid+20 ng/mL FGF7+50 ng/mL NOGGIN for 4 days, followed by DMEM/F12+1% ITS supplement+10 ng/mL bFGF+10 mM nicotinamide+50 ng/mL exendin-4+ 10 ng/mL BMP4 for 7-9 days to generate cardiac cells (FIG. 12). While cardiac cells cars be isolated from other cells present in the culture, this method generates a sufficiently high percentage of cardiac cells that such isolation is not generally required. The resulting cells can be used in vitro or in vivo for screening bioactive molecules for the study of heart disease or for the development of therapeutics for heart disease. The resulting cells can also be used for cardiotoxicity screening.

Example 16 Personalized Cell-Replacement Therapy for Ischemic Cardiomyopathy Comprising Reprogrammed Cells Patient skin cells are reprogrammed to cardiac cells according to Example 15. Cells are then enzymatically released from the culture vessel, and between about $1\times10^6$ and about $1\times10^7$ cells are injected into the pericardium or between about $1\times10^3$ and about $10\times10^5$ cells are injected into one or more coronary arteries. Cells engraft, and additional injections are performed as necessary.

Example 17 Personalized Cell-Replacement Therapy for Blood Disease Comprising Reprogrammed Cells Cells are reprogrammed according to Example 11 or Example 12, and are then cultured in IMDM+0.5% HSA+ 1×ITS supplement+450 µM monothioglycerol+2 mM L-glutamine+1× non-essential amino acids+50 ng/mL BMP4+50 ng/mL VEGF+50 ng/mL bFGF for 6 days, followed by IMDM+0.5% HSA+1×ITS supplement+0.1 mM 2-mercaptoethanol+5 U/mL heparin+10 ng/mL TPO+25 ng/mL SCF+ 25 ng/mL FLT3L+10 ng/mL IL-3+10 ng/mL IL-6 for 8 days to generate hematopoietic cells. Alternatively, cells are reprogrammed according to Example 11 or Example 12, and are then re-plated on collagen IV and cultured in IMDM+ 0.5% HSA+1×ITS supplement+450 µM monothioglycerol+2 mM L-glutamine+1× non-essential amino acids+50 ng/mL BMP4+50 ng/mL VEGF+50 ng/mL bFGF for 6 days, followed by IMDM+0.5% HSA+1×ITS supplement+0.1 mM 2-mercaptoethanol+5 U/mL heparin+10 ng/mL TPO+ 25 ng/mL SCF+25 ng/mL FLT3L+10 ng/mL IL-3+10 ng/mL IL-6 for 8 days to generate hematopoietic cells. Alternatively, cells are reprogrammed according to Example 11 or Example 12, and are then cultured in 1:1 F12/IMDM+0.5% HSA+1×ITS supplement+4.5 µg/mL cholesterol+10 µg/mL cod liver oil fatty acids+25 µg/mL polyoxyethylenesorbitan monooleate+2 ng/mL D-α-tocopherol acetate+450 µM monothioglycerol+2 mM L-glutamine+25 ng/mL BMP4+25 ng/mL VEGF+25 ng/mL bFGF+20 ng/mL SCF for 10 days to generate hematopoietic cells.

Example 18 Personalized Cell-Replacement Therapy for Blood Disease Comprising Reprogrammed Cells Patient skin cells are reprogrammed to hematopoietic cells according to Example 17. Cells are then released from the culture vessel, and between about $1\times10^5$ and about $1\times10^7$ cells/kg patient body weight are infused into a main vein over a period of several hours.

Example 19 Retinal Disease Models for Screening Bioactive Molecules

Cells are reprogrammed according to Example 11 or Example 12, and are then cultured in DMEM/F12+0.2% HSA+0.5× N2 supplement+0.5× B27 supplement 7 days to generate retinal cells. The resulting cells can be used in vitro or in vivo for screening bioactive molecules for the study of retinal disease or for the development of therapeutics for retinal disease.

Example 20 Personalized Cell-Replacement Therapy for Macular Degeneration Comprising Reprogrammed Cells Patient skin cells are reprogrammed to retinal cells according to Example 15. Cells are then enzymatically released from the culture vessel, and between about $1\times10^4$ and about $1\times10^5$ cells are injected into or below the retina. Cells engraft, and additional injections are performed as necessary.

REFERENCES

1. Barker A method for the deionization of bovine serum albumin. *Tissue Culture Association* (1975).
2. Droge, J. H., Janssen, L. H. & Wilting, J. A comparative study of some physico-chemical properties of human serum albumin samples from different sources—I. Some physico-chemical properties of isoionic human serum albumin solutions. *Biochem Pharmacol* 31, 3775-3779 (1982).
3. Ng, E. S., Davis, R., Stanley, E. G. & Elefanty, A. G. A protocol describing the use of a recombinant protein-based, animal product-free medium (APEL) for human embryonic stem cell differentiation as spin embryoid bodies, *Nat Protoc* 3, 768-776 (2008).
4. Garcia-Gonzalo, F. R. & Izpisua Belmonte, J. C. Albumin-associated lipids regulate human embryonic stem cell self-renewal *PLoS One* 3, e1384 (2008).
5. Takahashi, K. & Yanianaka. S. Induction of pluripotent stem cells from mouse embryonic and adult fibroblast cultures by defined factors. *Cell* 126, 663-676 (2006).
6. Okita, K., Ichisaka, T, & Yamanaka, S. Generation of germline-competent induced pluripotent stem cells. *Nature* 448, 313-317 (2007).
7. Wernig, M. et al. In vitro reprogramming of fibroblasts into a pluripotent ES-cell-like state. *Nature* 448, 318-324 (2007).
8. Takahashi, R, et al. Induction of pluripotent stem cells from adult human fibroblasts by defined factors. *Cell* 131, 861-872 (2007).
9. Yu, J. et al. Induced pluripotent stem cell fines derived from human somatic cells. *Science* 318, 1917-1920 (2007).
10. Zhou, H. et al. Generation of induced pluripotent stem cells using recombinant proteins. *Cell Stem Cell* 4, 381-384 (2009).
11. Kim, D. et al. Generation of human induced pluripotent stem cells by direct delivery of reprogramming proteins, *Cell Stem Cell* 4, 472-476 (2009).
12. Angel, M., In Electrical Engineering and Computer Science, Vol. Master of Science in Electrical Engineering 13. Angel, M. & Yanik, M. F. Innate immune suppression enables frequent transfection with RNA encoding reprogramming proteins. *PLoS ONE* 5, 1-7 (2010).
14. Warren, L, et al. Highly efficient reprogramming to pluripotency and directed differentiation of human cells with synthetic modified mRNA. *Cell Stem Cell* 7, 618-630 (2010).
15. Angel, M, in Electrical Engineering and Computer Science, Vol Doctor of Philosophy in Electrical Engineering and Computer Science 89 (Massachusetts Institute of Technology, Cambridge, Mass.; 2011).
16. Efe, J. A. et al Conversion of mouse fibroblasts into cardiornyoeytes using a direct reprogramming strategy. *Nat Cell Biol* 13, 215-222 (2011).
17. Goldberg, I. H. & Rabinowitz, M. The enzymic synthesis of pseudoundine triphosphate, *Biochim Biophys Acta* 54, 202-204 (1961).
18. Goldberg, I. H, Ribonucleic acid synthesis in nuclear extracts of mammalian cells grown in suspension culture; effect of ionic strength and surface-active agents. *Biochim Biophys Acta* 51, 201-204 (1961).
19. Goldberg, I. H. & Rabinowitz, M. The incorporation of 5-ribosyluracil triphosphate into RNA its nuclear extracts of mammalian cells. *Biochem Biophys Res Commun* 6, 394-398 (1961).
20. Kahan, F. M. & Hurwitz, J. The role of deoxyribonucleic acid in ribonucleic acid synthesis, IV. The incorporation of pyrimidine and purine analogues into ribonucleic acid. *J. Biol Chem* 237, 3778-3785 (1962).
21. Davis, D. R. Stabilization of RNA stacking by pseudoundine. *Nucleic Acids Res* 23, 5020-5026 (3995).
22. Kariko, K., Muramatsu, H., Ludwig, J. & Weissmait, D. Generating the optimal mRNA for therapy: HPLC purification eliminates immune activation and improves translation of nucleoside-modified, protein-encoding mRNA, *Nucleic Acids Res* 39, e142 (2011).
23. Xie, C. Q., Lin, G., Luo, K. L., Luo, S. W. & Lu, G. X. Newly expressed proteins of mouse embryonic fibroblasts irradiated to be inactive, *Biochem Biophys Res Commun* 315, 581-588 (2004).
24. Gurung, A., Uddin, F., Hill, R. P., Ferguson, P. C. & Ahuan, B. A. Beta-catenin is a mediator of the response of fibroblasts to irradiation. *Am J Pathol* 174, 248-255 (2009).
25. Shimizu, H. et al. Transformation by Wnt family proteins correlates with regulation of beta-catenin. *Cell Growth Differ* 8, 1349-1358 (1997).
26. You, Z. et al, Wnt signaling promotes oncogenic transformation by inhibiting c-Myc-induced apoptosis, *J Cell Biol* 157, 429-440 (2002).
27. Liu, J. et al. A small-molecule agonist of the Wnt signaling pathway, *Angew Chem Int Ed Engl* 44, 1987-1990 (2005).
28. Kim, J. B, et al., Pluripotent stem cells induced from adult neural stem cells by reprogramming with two factors. *Nature* 454, 646-650 (2008).
29. Kim, J. B. et al. Oct4-induced pluripotency in adult neural stem cells. *Cell* 136, 411-419 (2009).
30. Lin, T. et al. A chemical platform for improved induction of human IPSCs. *Nat Methods* 6, 805-808 (2009).
31. Watanabe, K. et al. A ROCK inhibitor permits survival of dissociated human embryonic stem cells, *Nat Biotechnol* 25, 681-686 (2007).
32. Chen, G. et al. Chemically defined conditions for human iPSC derivation and culture. *Nat Methods* 8, 424-429 (2011).
33. Braam, S. R. et al. Recombinant vitronectin is a functionally defined substrate that supports human embryonic stem cell self-renewal via alphavbeta5 integrin. *Stem Cells* 26, 2257-2265 (2008).
34. Bolli, R. et al. Cardiac stem cells in patients with ischaemic cardiomyopathy (SCIPIO); initial results of a randomised phase I trial. *Lancet* 378, 1847-1857 (2011).
35. Schwartz, S. D. et al. Embryonic stem cell trials for macular degeneration: a preliminary report. *Lancet* 713-720 (2012).
36. Rossi, A. et al. Anti-inflammatory cyclopentenone prostaglandins are direct inhibitors of IkappaB kinase. *Nature* 403, 103-108 (2000).
37. Yakubov, E., Rechavi, G., Rozenblatt, S. & Givol, D. Reprogramming of human fibroblasts to pluripotent stein cells using mRNA of four transcription factors. *Biochem Biophys Res Commun* 394, 189-193 (2010).
38. Plews, J. R. et al. Activation of pluripotency genes in human fibroblast cells by a novel mRNA based approach. *PLoS One* 5, e14397 (2011).
39. Arnold, A. et al. Reprogramming of Human Huntington Fibroblasts Using mRNA, ISRN *Cell Biology* 2012, 12 (2012).
40. Liu, T. et al. High Efficiency of Reprogramming CD34 (+) Cells Derived from Human Amniotic Fluid into Induced Pluripotent Stem Cells with Oct4, *Stem Cells Dev* (2012).
41. Young, M. A, et al. Background Mutations in Parental Cells Account for Most of the Genetic Heterogeneity of Induced Pluripotent Stem Cells, *Cell Stem Cell* (2012).
42. Ludwig, T. E. et al. Feeder-independent culture of human embryonic stem cells. *Nat Methods* 3, 637-646 (2006).
43. Ludwig, T. E, et al. Derivation of human embryonic stem cells in defined conditions, *Nat Biotechnol* 24, 185-187 (2006).
44. Anderson, B. R., Kariko, K, & Weissman, D. Nucleofection induces transient elF2alpha phosphorylation by GCN2 and PERK. *Gene Ther* (2012).

What is claimed is:

1. A method for reprogramming a differentiated cell to a less differentiated state, comprising:
   (a) providing a differentiated cell;
   (b) culturing the differentiated cell; and
   (c) transfecting the differentiated cell with one or more synthetic RNA molecules,
      wherein the one or more synthetic RNA molecules include at least one RNA molecule encoding one or more reprogramming factors;
      wherein the transfecting results in the cell expressing the one or more reprogramming factors to result in the cell being reprogrammed to a less differentiated state; and
      wherein step (c) is performed without using irradiated human neonatal fibroblast feeder cells and occurs in the presence of a medium containing ingredients that support reprogramming of the cell to a less differentiated state.

2. The method of claim 1, wherein the differentiated cell is derived from a biopsy.

3. The method of claim 2, wherein the differentiated cell is derived from a dermal punch biopsy sample.

4. The method of claim 1, wherein the differentiated cell is from a human subject.

5. The method of claim 1, wherein the differentiated cell is a skin cell.

6. The method of claim 1, further comprising contacting the cell with at least one member of the group: poly-L-lysine, poly-L-ornithine, RGD peptide, fibronectin, vitronectin, collagen, and laminin.

7. The method of claim 1, wherein the one or more synthetic RNA molecules contain at least one of a pseudouridine or a 5-methylcytidine residue.

8. The method of claim 1, wherein the medium is substantially free of immunosuppressants.

9. A method for reprogramming a non-pluripotent cell, comprising:
   (a) providing a non-pluripotent cell;
   (b) culturing the non-pluripotent cell; and
   (c) transfecting the non-pluripotent cell with one or more synthetic RNA molecules,
      wherein the one or more synthetic RNA molecules include at least one RNA molecule encoding one or more reprogramming factors;
      wherein the transfecting results in the cell expressing the one or more reprogramming factors to result in the cell being reprogrammed; and
      wherein step (c) is performed without using irradiated human neonatal fibroblast feeder cells and occurs in the presence of a medium containing ingredients that support reprogramming of the cell.

10. The method of claim 9, wherein the non-pluripotent cell is derived from a biopsy.

11. The method of claim 10, wherein the non-pluripotent cell is derived from a dermal punch biopsy sample.

12. The method of claim 9, wherein the non-pluripotent cell is from a human subject.

13. The method of claim 9, wherein the non-pluripotent cell is a skin cell.

14. The method of claim 9, further comprising contacting the cell with at least one member of the group: poly-L-lysine, poly-L-ornithine, RGD peptide, fibronectin, vitronectin, collagen, and laminin.

15. The method of claim 9, wherein the one or more synthetic RNA molecules contain at least one of a pseudouridine or a 5-methylcytidine residue.

16. The method of claim 9, wherein the medium is substantially free of immunosuppressants.

* * * * *